US012590105B2

(12) United States Patent
Hyman et al.

(10) Patent No.: US 12,590,105 B2
(45) Date of Patent: Mar. 31, 2026

(54) KRas G12C INHIBITORS

(71) Applicant: Eli Lilly and Company, Indianapolis, IN (US)

(72) Inventors: David Michael Hyman, Westport, CT (US); Gregory Lawrence Lackner, Indianapolis, IN (US); Sheng-Bin Peng, Carmel, IN (US); Bree Leigh Richey, Indianapolis, IN (US); Chong Si, Zionsville, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 504 days.

(21) Appl. No.: 18/255,713

(22) PCT Filed: Nov. 24, 2021

(86) PCT No.: PCT/US2021/060715

§ 371 (c)(1),
(2) Date: Jun. 2, 2023

(87) PCT Pub. No.: WO2022/119748

PCT Pub. Date: Jun. 9, 2022

(65) Prior Publication Data

US 2024/0025916 A1 Jan. 25, 2024

Related U.S. Application Data

(60) Provisional application No. 63/121,272, filed on Dec. 4, 2020.

(51) Int. Cl.

| | |
|---|---|
| ***C07D 498/04*** | (2006.01) |
| ***A61K 31/4985*** | (2006.01) |
| ***A61K 45/06*** | (2006.01) |
| ***A61P 35/00*** | (2006.01) |

(52) U.S. Cl.
CPC ............ *C07D 498/04* (2013.01); *A61K 45/06* (2013.01)

(58) Field of Classification Search
CPC .............................. C07D 498/04; A61K 45/06
See application file for complete search history.

(56) References Cited

FOREIGN PATENT DOCUMENTS

| | | | |
|---|---|---|---|
| WO | 2020/178282 A | 9/2020 | |
| WO | WO-2020178282 A1 * | 9/2020 | ........... C07D 498/14 |

OTHER PUBLICATIONS

International Search Report and Written Opinion in International Application No. PCT/US2021/060715, dated Feb. 14, 2022, 11 pages.

* cited by examiner

*Primary Examiner* — Jeffrey S Lundgren
*Assistant Examiner* — Paul Randall Gauger
(74) *Attorney, Agent, or Firm* — Stefan Ochiana

(57) ABSTRACT

The present disclosure provides compounds of the formula:

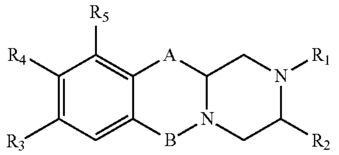

where $R_1$, $R_2$, $R_3$, $R_4$, $R_5$, A, and B are as described herein, pharmaceutically acceptable salts thereof, and methods of using these compounds and salts for treating patients for cancer.

24 Claims, No Drawings

KRas G12C INHIBITORS

This application is the national stage of PCT international application number PCT/US2021/060715, filed Nov. 24, 2021, this PCT international application claims the benefit of U.S. Provisional Application No. 63/121,272, filed Dec. 4, 2020, which is herein incorporated by reference in its entirety.

The present disclosure relates to novel tricyclic heterocyclic compounds and pharmaceutically acceptable salts thereof, pharmaceutical compositions including the tricyclic heterocyclic compounds and salts, and methods of using the compounds and salts to treat cancers such as lung cancer, colorectal cancer, pancreatic cancer, bladder cancer, cervical cancer, endometrial cancer, ovarian cancer, cholangiocarcinoma or esophageal cancer.

The MAPK/ERK signaling pathway relays extracellular stimuli to the nucleus, thereby regulating diverse cellular responses including cell proliferation, differentiation, and apoptosis. KRas protein is an initiator of the MAPK/ERK signaling pathway and functions as a switch responsible for inducing cell division. In its inactive state, KRas binds guanosine diphosphate (GDP), effectively sending a negative signal to suppress cell division. In response to an extracellular signal, KRas is allosterically activated allowing for nucleotide exchange of GDP for guanosine triphosphate (GTP). In its GTP-bound active state, KRas recruits and activates proteins necessary for the propagation of growth factor induced signaling, as well as other cell signaling receptors. Examples of the proteins recruited by KRas-GTP are c-Raf and PI3-kinase. KRas, as a GTP-ase, converts the bound GTP back to GDP, thereby returning itself to an inactive state, and again propagating signals to suppress cell division. KRas gain of function mutations exhibit an increased degree of GTP binding and a decreased ability to convert GTP into GDP. The result is an increased MAPK/ERK signal which promotes cancerous cell growth. Missense mutations of KRas at codon 12 are the most common mutations and markedly diminish GTPase activity.

Oncogenic KRas mutations have been identified in approximately 30% of human cancers and have been demonstrated to activate multiple downstream signaling pathways. Despite the prevalence of KRas mutations, it has been a difficult therapeutic target. (Cox, A. D. *Drugging the Undruggable RAS: Mission Possible*? Nat. Rev. Drug Disc. 2014, 13, 828-851; Pylayeva-Gupta, y et al. *RAS Oncogenes: Weaving a Tumorigenic Web*. Nat. Rev. Cancer 2011, 11, 761-774).

WO2015/054572 and WO2016/164675 disclose certain quinazoline derivatives capable of binding to KRas G12C. WO2016/044772 also discloses methods of using such quinazoline derivatives. WO2020/0081282 discloses KRas G12C inhibitors. WO2018/206539 and WO2020/178282 disclose certain heteroaryl compounds capable of binding to KRas G12C RAS proteins.

There remains a need to provide alternative, small molecule KRas inhibitors. In particular, there is a need to provide more potent, orally deliverable KRas inhibitors that are useful for treating cancer. More particularly, there is a need to provide small molecule inhibitors that specifically inhibit KRas GTP activity. There is also a need to provide small molecule KRas inhibitors that exhibit greater efficacy at the same or reduced KRas inhibitory activity. Further, there is a desire to provide KRas inhibitors that exhibit better pharmacokinetic/pharmacodynamic properties. Also, there is a need to provide more potent KRas inhibitors that exhibit increased efficacy with reduced or minimized untoward or undesired effects. The present disclosure addresses one or more of these needs by providing novel KRas inhibitors.

The present disclosure provides a compound of Formula I:

Formula I

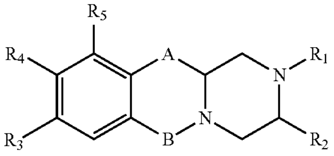

or a pharmaceutically acceptable salt thereof, wherein:

A is $-OCH_2-$, $-N(R_6)CH_2-$, $-OCH_2CH_2-$, $-N(R_6)CH_2CH_2-$, $-CH_2OCH_2-$, or $-CH_2N(R_6)CH_2-$;

B is $-CH_2-$ or $-C(O)-$;

$R_1$ is $-CN$, $-C(O)C{\equiv}CR_8$, or a group of the formula

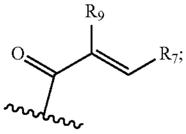

$R_2$ is H, methyl, or $-CH_2CN$;

$R_3$ and $R_5$ are each independently H, halogen, cyclopropyl, $-C_{1-3}$ alkyl-cyclopropyl, $-C_{1-6}$ alkyl optionally substituted 1-3 times with $R_{10}$, or $-O-C_{1-6}$ alkyl optionally substituted 1-3 times with $R_{10}$;

$R_4$ is a group of the formula

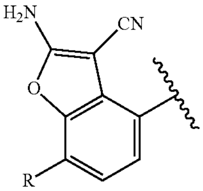,
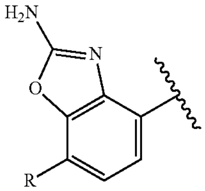,
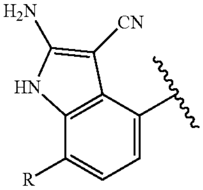,
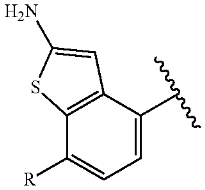,
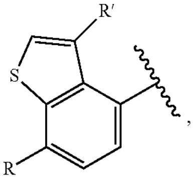,
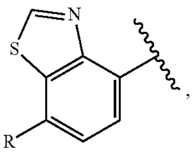, or
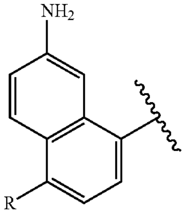;

R is H, halogen, or —$C_{1-6}$ alkyl optionally substituted 1-3 times with $R_{10}$;

R' is H, or —$C_{1-6}$ alkyl;

$R_6$ is H or —$C_{1-6}$ alkyl optionally substituted 1-3 times with $R_{10}$;

$R_7$ is H, halogen, —$NR_{11}R_{12}$, —$CH_2NR_{11}R_{12}$, —$C_{2-6}$ alkyl optionally substituted 1-3 times with $R_{10}$ or —$NR_{13}R_{14}$, cyclopropyl, —$C_{1-3}$ alkyl cyclopropyl, or —O—$C_{1-6}$ alkyl optionally substituted 1-3 times with $R_{10}$ or —$NR_{13}R_{14}$;

$R_8$ is H, —$C_{1-4}$ alkyl optionally substituted 1-3 times with $R_{10}$, or —$C_{3-6}$ cycloalkyl optionally substituted 1-3 times with $R_{10}$;

$R_9$ is H, halogen, —CN, $C_{3-6}$ cycloalkyl, —$C_{1-3}$ alkyl-$C_{3-6}$ cycloalkyl, or —$C_{1-6}$ alkyl optionally substituted 1-3 times with $R_{10}$;

$R_{10}$ is independently at each occurrence halogen, oxygen, hydroxy, —$C_{1-4}$ alkyl, or —O—$C_{1-4}$ alkyl;

$R_{11}$ and $R_{12}$ are each independently H, —$C_{1-4}$ alkyl, or —$C_{1-4}$ heteroalkyl, wherein $R_{11}$ and $R_{12}$ may combine to form a $C_{5-6}$ heterocycloalkyl; and $R_{13}$ and $R_{14}$ are each independently H or —$C_{1-4}$ alkyl.

As used herein, the term halogen means fluoro (F), chloro (Cl), bromo (Br), or iodo (I). As used herein, the term alkyl means saturated linear or branched-chain monovalent hydrocarbon radicals. Examples of "—$C_{1-6}$ alkyl" include, but are not limited to, methyl, ethyl, propyl, 1-propyl, isopropyl, butyl, isobutyl, pentyl, and hexyl. As used herein, the term "—$C_{1-4}$ heteroalkyl" means saturated linear or branched-chain monovalent hydrocarbon radicals containing one to four carbon atoms and at least one heteroatom. As used herein, the term "—$C_{3-6}$ cycloalkyl" means saturated monovalent cyclic molecules with three to six carbon atoms. Examples of cycloalkyl groups include, but are not limited to, cyclopropyl, cyclobutyl, cyclopentyl, and cyclohexyl.

Regarding $R_{11}$ and $R_{12}$, the two groups may combine with the nitrogen they are attached to when chemistry allows to form a $C_{5-6}$ heterocycloalkyl. As used herein, the term "—$C_{5-6}$ heterocycloalkyl" means saturated monovalent cyclic molecules with four to five carbon atoms and at least one heteroatom. Examples of heterocycloalkyl groups include, but are not limited to, morpholine, pyrrolidine, piperidine, imidazolidine, pyrazolidine, and piperazine.

An embodiment disclosed herein provides a compound of Formula Ia

Formula Ia

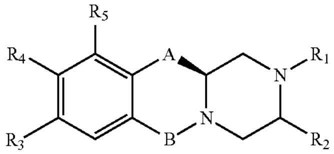

where $R_1$, $R_2$, $R_3$, $R_4$, $R_5$, A, and B are as defined above, or a pharmaceutically acceptable salt thereof.

An embodiment disclosed herein provides a compound of Formula I or Ia wherein A is —$OCH_2$—, —$N(R_6)CH_2$—, —$OCH_2CH_2$—, or —$N(R_6)CH_2CH_2$—, or a pharmaceutically acceptable salt thereof. Another embodiment provides a compound of Formula I or Ia wherein A is —$OCH_2$— or —$OCH_2CH_2$—, or a pharmaceutically acceptable salt thereof. Another embodiment provides a compound of Formula I or Ia wherein A is —$OCH_2CH_2$—, or a pharmaceutically acceptable salt thereof.

A further embodiment provides a compound of Formula I or Ia wherein B is —C(O)—, or a pharmaceutically acceptable salt thereof.

A further embodiment provides a compound of Formula I or Ia wherein $R_1$ is —CN or —$C(O)C{\equiv}CR_8$, or a pharmaceutically acceptable salt thereof. Another embodiment provides a compound of Formula I or Ia wherein $R_1$ is a group of the formula

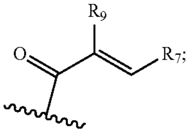

or a pharmaceutically acceptable salt thereof.

A further embodiment provides a compound of Formula I or Ia wherein $R_2$ is H or methyl, or a pharmaceutically acceptable salt thereof. Another embodiment provides a compound of Formula I or Ia wherein $R_2$ is H, or a pharmaceutically acceptable salt thereof.

A further embodiment provides a compound of Formula I or Ia wherein $R_3$ is H, halogen, preferably F or Cl, methyl, methoxy, ethyl, isopropyl, or cyclopropyl, or a pharmaceutically acceptable salt thereof. Another embodiment provides a compound of Formula I or Ia wherein $R_3$ is halogen, preferably F or Cl, or a pharmaceutically acceptable salt thereof.

A further embodiment provides a compound of Formula I or Ia wherein $R_4$ is a group of the formula

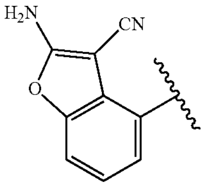
,
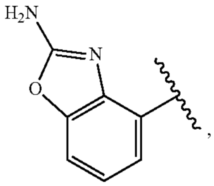
,
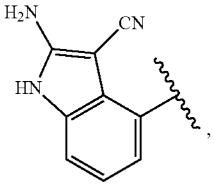
,
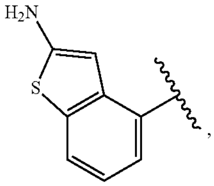
,
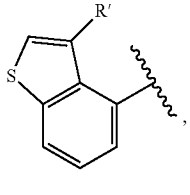
,
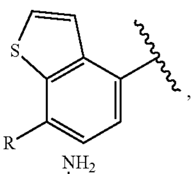
,
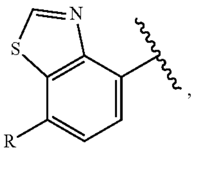
, or
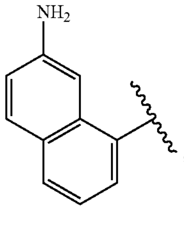
;

or a pharmaceutically acceptable salt thereof. Another embodiment provides a compound of Formula I or Ia wherein $R_4$ is a group of the formula

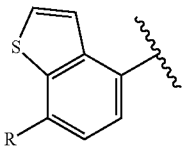,
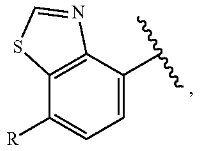, or
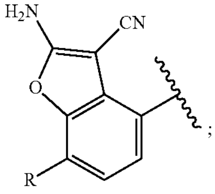;

or a pharmaceutically acceptable salt thereof. Another embodiment provides a compound of Formula I or Ia wherein $R_4$ is a group of the formula

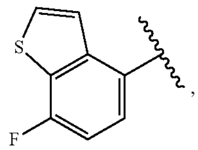,
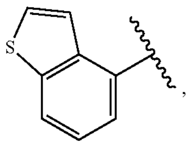,
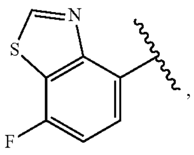, or
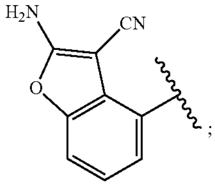;

or a pharmaceutically acceptable salt thereof.

An embodiment provides a compound of Formula I or Ia wherein R is H or halogen, preferably F, or a pharmaceutically acceptable salt thereof.

An embodiment provides a compound of Formula I or Ia wherein $R_5$ is H, halogen, $CHF_2$, $CH_2F$, $CH_2OH$, or $CH_2OCH_3$, or a pharmaceutically acceptable salt thereof. A further embodiment provides a compound of Formula I or Ia wherein $R_5$ is halogen, preferably Cl, or a pharmaceutically acceptable salt thereof.

A further embodiment provides a compound of Formula I or Ia wherein $R_6$ is H or $CH_3$, or a pharmaceutically acceptable salt thereof.

A further embodiment provides a compound of Formula I or Ia wherein $R_9$ is H, F, Cl, $—CH_2F$, $—CF_3$, or $—CH_2OH$, or a pharmaceutically acceptable salt thereof. A further embodiment provides a compound of Formula I or Ia wherein $R_9$ is H, or a pharmaceutically acceptable salt thereof.

An embodiment provides a compound of Formula I or Ia wherein $R_7$ is H, $—CHF_2$, $—CH_2F$, $—CH_2OH$, $—CH_2OCH_3$, $—CH_2N(CH_3)_2$, or $—CH_2$-morpholine, or a pharmaceutically acceptable salt thereof. Another embodiment provides a compound of Formula I or Ia wherein $R_7$ is H, or a pharmaceutically acceptable salt thereof.

An embodiment provides a compound of Formula I or Ia wherein $R_9$ is H and $R_7$ is H, $—CHF_2$, $—CH_2F$, $—CH_2OH$, $—CH_2OCH_3$, $—CH_2N(CH_3)_2$, or $—CH_2$-morpholine, or a pharmaceutically acceptable salt thereof.

Another embodiment provides a compound of Formula I or Ia wherein $R_9$ is H, F, Cl, $—CH_2F$, $—CF_3$, or $—CH_2OH$ and $R_7$ is H, or a pharmaceutically acceptable salt thereof.

An embodiment provides a compound of Formula I or Ia wherein $R_7$ and $R_9$ are both H, or a pharmaceutically acceptable salt thereof.

An embodiment provides a compound of Formula I or Ia wherein $R_1$ is —CN or $—C(O)C{\equiv}CR_8$ and $R_8$ is H, methyl, $—CH_2F$, or $—CH_2OH$, or a pharmaceutically acceptable salt thereof.

An embodiment provides a compound of Formula I or Ia wherein $R_1$ is a group of the formula

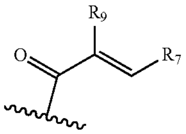

and $R_7$ is H, $—CHF_2$, $—CH_2F$, $—CH_2OH$, $—CH_2OCH_3$, $—CH_2N(CH_3)_2$, or $—CH_2$-morpholine, or a pharmaceutically acceptable salt thereof.

An embodiment provides a compound of Formula I or Ia wherein $R_1$ is a group of the formula

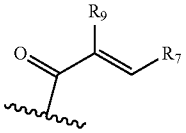

and $R_9$ is H, F, Cl, $CHF_2$, $CF_3$, or $CH_2OH$, or a pharmaceutically acceptable salt thereof.

An embodiment provides a compound of Formula I or Ia wherein $R_1$ is a group of the formula

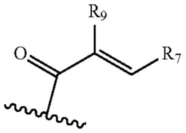

and $R_7$ and $R_9$ are both H, or a pharmaceutically acceptable salt thereof.

An embodiment provides a compound of Formula I or Ia wherein $R_1$ is a group of the formula

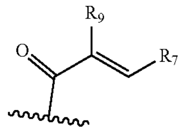

and $R_7$ is tert-butyl and $R_9$ is —CN, or a pharmaceutically acceptable salt thereof.

An embodiment provides a compound of Formula I or Ia wherein A is $—OCH_2—$, $—N(R_6)CH_2—$, $—OCH_2CH_2—$, or $—N(R_6)CH_2CH_2—$, and B is —C(O)—, or a pharmaceutically acceptable salt thereof.

An embodiment provides a compound of Formula I or Ia wherein A is $—OCH_2—$ or $—OCH_2CH_2—$ and B is —C(O)—, or a pharmaceutically acceptable salt thereof.

An embodiment provides a compound of Formula I or Ia wherein A is $—OCH_2CH_2—$ and B is $—C(O)—$, or a pharmaceutically acceptable salt thereof.

An embodiment provides a compound of Formula I or Ia wherein A is $—OCH_2—$, $—N(R_6)CH_2—$, $—OCH_2CH_2—$, or $—N(R_6)CH_2CH_2—$; B is C(O); and $R_2$ is H or $—CH_3$; or a pharmaceutically acceptable salt thereof.

An embodiment provides a compound of Formula I or Ia wherein A is $—OCH_2—$ or $—OCH_2CH_2—$; B is $—C(O)—$; and $R_2$ is H or methyl; or a pharmaceutically acceptable salt thereof.

An embodiment provides a compound of Formula I or Ia wherein A is $—OCH_2CH_2—$, B is $—C(O)—$, and $R_2$ is H or methyl, or a pharmaceutically acceptable salt thereof.

An embodiment provides a compound of Formula I or Ia wherein A is $—OCH_2—$, $—N(R_6)CH_2—$, $—OCH_2CH_2—$, or $—N(R_6)CH_2CH_2—$; B is $—C(O)—$; and $R_2$ is H; or a pharmaceutically acceptable salt thereof.

An embodiment provides a compound of Formula I or Ia wherein A is $—OCH_2—$ or $—OCH_2CH_2—$; B is $—C(O)—$; and $R_2$ is H; or a pharmaceutically acceptable salt thereof.

An embodiment provides a compound of Formula I or Ia wherein A is $—OCH_2CH_2—$, B is $—C(O)—$, and $R_2$ is H, or a pharmaceutically acceptable salt thereof.

An embodiment provides a compound of Formula I or Ia wherein A is $—OCH_2CH_2—$ and $R_2$ is H or methyl, or a pharmaceutically acceptable salt thereof.

An embodiment provides a compound of Formula I or Ia wherein A is $—OCH_2CH_2—$ and $R_2$ is H, or a pharmaceutically acceptable salt thereof.

An embodiment provides a compound of Formula I or Ia wherein B is $—C(O)—$ and $R_2$ is H or methyl, or a pharmaceutically acceptable salt thereof.

An embodiment provides a compound of Formula I or Ia wherein B is $—C(O)—$ and $R_2$ is H, or a pharmaceutically acceptable salt thereof.

An embodiment provides a compound of Formula I or Ia wherein $R_3$ and $R_5$ are each independently selected from H, halogen, and methyl, or a pharmaceutically acceptable salt thereof.

An embodiment provides a compound of Formula I or Ia wherein $R_3$ or $R_5$ are halogen, preferably F or Cl, or a pharmaceutically acceptable salt thereof.

An embodiment provides a compound of Formula I or Ia wherein A is $—OCH_2—$ or $—OCH_2CH_2—$; B is $—C(O)—$; $R_1$ is a group of the formula

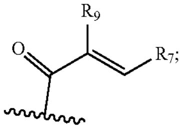

$R_2$ is H or methyl; $R_3$ and $R_5$ are each H, F, Cl or methyl; $R_4$ is a group of the formula

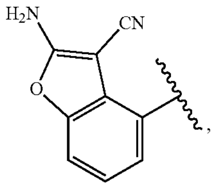
,
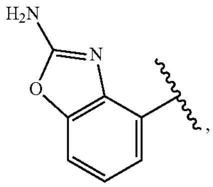
,
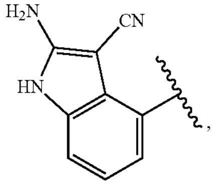
,
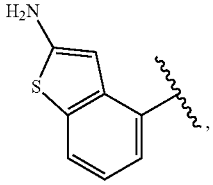
,
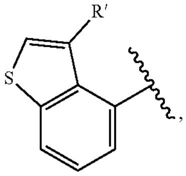
,
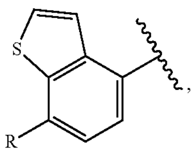
,
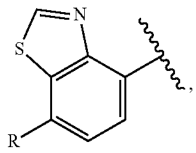
, or
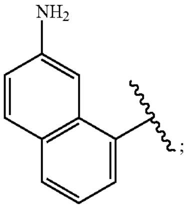
;

$R_6$ is H or methyl; $R_7$ and $R_9$ are both H; R is H or F; R' is H or methyl; or a pharmaceutically acceptable salt thereof.

An embodiment provides a compound of Formula I or Ia wherein A is $—OCH_2CH_2—$; B is $—C(O)—$; $R_1$ is a group of the formula

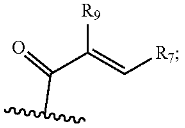

$R_2$, $R_7$, and $R_9$ are each H; $R_4$ is a group of the formula

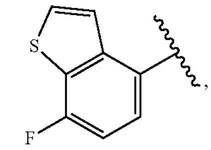
,
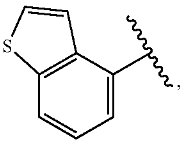
,
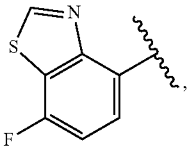
, or
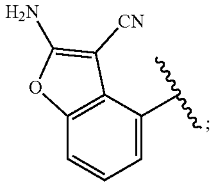
;

$R_3$ and $R_5$ are each halogen; or a pharmaceutically acceptable salt thereof.

An embodiment provides a compound selected from any one of Formulae II-VI below:

Formula II

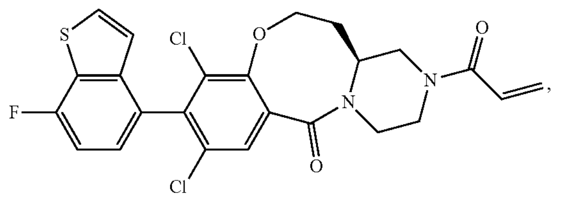

Formula III

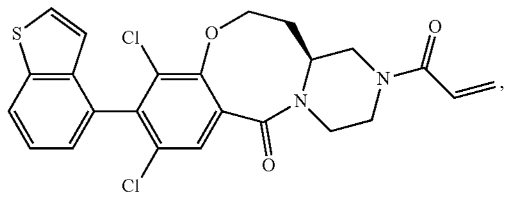

Formula IV

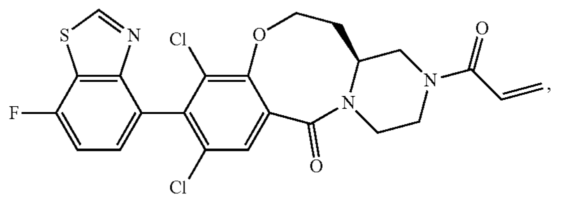

Formula V

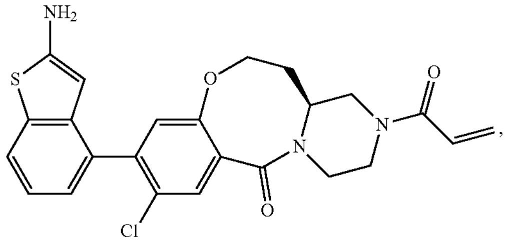

, and

Formula VI

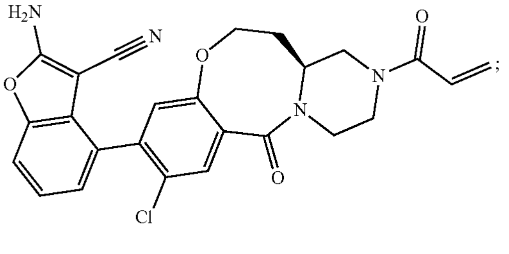

or a pharmaceutically acceptable salt thereof.

Another embodiment provides a compound of Formula II, or a pharmaceutically acceptable salt thereof.

Another embodiment provides a compound of Formula III, or a pharmaceutically acceptable salt thereof.

Another embodiment provides a compound of Formula IV, or a pharmaceutically acceptable salt thereof.

Another embodiment provides a compound of Formula V, or a pharmaceutically acceptable salt thereof.

Another embodiment provides a compound of Formula VI, or a pharmaceutically acceptable salt thereof.

Another embodiment provides a pharmaceutical composition comprising a compound according to any one of Formulae I-VI, or a pharmaceutically acceptable salt thereof, and a pharmaceutically acceptable carrier, diluent, or excipient.

Another embodiment provides a method of treating cancer, comprising administering to a patient in need thereof, an effective amount of a compound according to any one of Formulae I-VI, or a pharmaceutically acceptable salt thereof. In various embodiments, the cancer is lung cancer, colorectal cancer, pancreatic cancer, bladder cancer, cervical cancer, endometrial cancer, ovarian cancer, cholangiocarcinoma, or esophageal cancer. In preferred embodiments, the cancer is non-small cell lung cancer, pancreatic cancer, or colorectal cancer. In still more preferred embodiments, the cancer is non-small cell lung cancer.

Another embodiment provides for a method of treating cancer, comprising administering to a patient in need thereof, an effective amount of a compound according to any one of Formulae I-VI, or a pharmaceutically acceptable salt thereof, in which the cancer has one or more cells that express a mutant KRas G12C protein. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In yet another embodiment, the cancer is mutant pancreatic cancer in which the cancer has one or more cells that express a KRas G12C mutant protein. Another embodiment provides for a method of treating KRas G12C mutant bearing cancers of other origins.

Another embodiment provides a method of treating a patient with a cancer that has a KRAS G12C mutation comprising administering to a patient in need thereof an effective amount of a compound according to any one of Formulae I-VI, or a pharmaceutically acceptable salt thereof.

Another embodiment provides a method of modulating a mutant KRas G12C enzyme in a patient in need thereof, by administering a compound according to any one of Formulae I-VI, or a pharmaceutically acceptable salt thereof. Preferably the method comprises inhibiting a human mutant KRas G12C enzyme.

Another embodiment provides a method of treating cancer in a patient in need thereof, wherein the patient has a cancer that was determined to express the KRas G12C mutant protein. The method comprises administering to a patient an effective amount of a compound according to any one of Formulae I-VI, or a pharmaceutically acceptable salt thereof. The G12C mutational status of one or more cancer cells can be determined by a number of assays known in the art. Typically, one or more biopsies containing one or more cancer cells are obtained, and subjected to sequencing and/or polymerase chain reaction (PCR). Circulating cell-free DNA can also be used, e.g. in advanced cancers. Non-limiting examples of sequencing and PCR techniques used to determine the mutational status (e.g. G12C mutational status, in one or more cancer cells or in circulating cell-free DNA) include direct sequencing, next-generation sequencing, reverse transcription polymerase chain reaction (RT-PCR), multiplex PCR, and pyrosequencing and multi-analyte profiling.

Another embodiment provides a compound or a pharmaceutically acceptable salt thereof according to any one of Formulae I-VI for use in therapy. Another embodiment provides the compound or a pharmaceutically acceptable salt thereof, for use in treating cancer. Preferably, the cancer is lung cancer, colorectal cancer, pancreatic cancer, bladder cancer, cervical cancer, endometrial cancer, ovarian cancer, cholangiocarcinoma, or esophageal cancer. In preferred embodiments the cancer is non-small cell lung cancer, pancreatic cancer, or colorectal cancer. In still more preferred embodiments, the cancer is non-small cell lung cancer. In other embodiments, the cancer has one or more cancer cells that express the mutant KRas G12C protein. Preferably, the cancer is selected from: KRas G12C mutant non-small cell lung cancer, KRas G12C mutant colorectal cancer, and KRas G12C mutant pancreatic cancer. In another embodiment, the cancer is non-small cell lung cancer, and one or more cells express KRas G12C mutant protein. In another embodiment, the cancer is colorectal cancer, and one or more cells express KRas G12C mutant protein. In another embodiment, the cancer is pancreatic cancer, and one or more cells express KRas G12C mutant protein. In another embodiment, the patient has a cancer that was determined to have one or more cells expressing the KRas G12C mutant protein prior to administration of the compound or a pharmaceutically acceptable salt thereof.

Another embodiment provides for the use of a compound according to any one of Formulae I-VI, or a pharmaceutically acceptable salt thereof, in the manufacture of a medicament for treating cancer. Preferably, the cancer is lung cancer, colorectal cancer, pancreatic cancer, bladder cancer, cervical cancer, endometrial cancer, ovarian cancer, cholangiocarcinoma, or esophageal cancer. In preferred embodiments, the cancer is non-small cell lung cancer, pancreatic cancer, or colorectal cancer. In still more preferred embodiments, the cancer is non-small cell lung cancer. In other embodiments, the cancer has one or more cancer cells that express the mutant KRas G12C protein. Preferably, the cancer is selected from KRas G12C mutant non-small cell lung cancer, KRas G12C mutant colorectal cancer, and KRas G12C mutant pancreatic cancer.

An embodiment provides a method of treating cancer, comprising administering to a patient in need thereof, an effective amount of a compound according to any one of Formulae I-VI, or a pharmaceutically acceptable salt thereof, and one or more of a PD-1 inhibitor, a PD-L1 inhibitor, a CDK4/CDK6 inhibitor, or a pharmaceutically acceptable salt thereof, an EGFR inhibitor, or a pharmaceutically acceptable salt thereof, an ERK inhibitor, or a pharmaceutically acceptable salt thereof a platinum agent, and pemetrexed, or a pharmaceutically acceptable salt thereof, in which the cancer has one or more cells that express a mutant KRas G12C protein. Another embodiment also provides a compound according to any one of Formulae I-VI, or a pharmaceutically acceptable salt thereof, for use in simultaneous, separate or sequential combination with one or more of a PD-1 or PD-L1 inhibitor, a CDK4/CDK6 inhibitor, or a pharmaceutically acceptable salt thereof, an EGFR inhibitor, or a pharmaceutically acceptable salt thereof, an ERK inhibitor, or a pharmaceutically acceptable salt thereof a platinum agent, and pemetrexed, or a pharmaceutically acceptable salt thereof, in the treatment of cancer. Another embodiment provides a combination comprising a compound according to any one of Formulae I-VI, or a pharmaceutically acceptable salt thereof, and one or more of a PD-1 or PD-L1 inhibitor, a CDK4/CDK6 inhibitor, or a pharmaceutically acceptable salt thereof, an EGFR inhibitor, or a pharmaceutically acceptable salt thereof, an ERK inhibitor, or a pharmaceutically acceptable salt thereof a platinum agent, and pemetrexed, or a pharmaceutically acceptable salt thereof, for simultaneous, separate, or sequential use in the treatment of cancer.

An embodiment provides a method of treating cancer, comprising administering to a patient in need thereof, an effective amount of a compound according to any one of Formulae I-VI, or a pharmaceutically acceptable salt thereof, and a PD-1 or PD-L1 inhibitor, in which the cancer has one or more cells that express a mutant KRas G12C protein. An embodiment also provides a compound according to any one of Formulae I-VI, or a pharmaceutically acceptable salt thereof, for use in simultaneous, separate or sequential combination with a PD-1 or PD-L1 inhibitor, in the treatment of cancer. An embodiment also provides a combination comprising a compound according to any one of Formulae I-VI, or a pharmaceutically acceptable salt thereof, and a PD-1 or PD-L1 inhibitor, for simultaneous, separate, or sequential use in the treatment of cancer. In another embodiment, the PD-1 or PD-L1 inhibitor is pembrolizumab. In another embodiment, the PD-1 or PD-L1 inhibitor is nivolumab. In another embodiment, the PD-1 or PD-L1 inhibitor is cemiplimab. In another embodiment, the PD-1 or PD-L1 inhibitor is sintilimab. In another embodiment, the PD-1 or PD-L1 inhibitor is atezolizumab. In another embodiment, the PD-1 or PD-L1 inhibitor is avelumab. In another embodiment, the PD-1 or PD-L1 inhibitor is durvalumab. In another embodiment, the PD-1 or PD-L1 inhibitor is lodapilimab. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. An embodiment comprises a method of treating KRas G12C mutant bearing cancers of other origins.

An embodiment provides a method of treating cancer, comprising administering to a patient in need thereof, an effective amount of a compound according to any one of Formulae I-VI, or a pharmaceutically acceptable salt thereof, and a CDK4/CDK6 inhibitor, or a pharmaceutically acceptable salt thereof, in which the cancer has one or more cells that express a mutant KRas G12C protein. An embodiment also provides a compound according to any one of Formulae I-VI, or a pharmaceutically acceptable salt thereof, for use in simultaneous, separate or sequential combination with a CDK4/CDK6 inhibitor, or a pharmaceutically acceptable salt thereof, in the treatment of cancer, in which the cancer has one or more cells that express a mutant KRas G12C protein. An embodiment also provides a combination comprising a compound according to any one of Formulae I-VI, or a pharmaceutically acceptable salt thereof, and a CDK4/CDK6 inhibitor, or a pharmaceutically acceptable salt thereof, for simultaneous, separate, or sequential use in the treatment of cancer, in which the cancer has one or more cells that express a mutant KRas G12C protein. In another embodiment, the CDK4/CDK6 inhibitor is abemaciclib. In another embodiment, the CDK4/CDK6 inhibitor is palbociclib. In another embodiment, the CDK4/CDK6 inhibitor is ribociclib. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. An embodiment comprises a method of treating KRas G12C mutant bearing cancers of other origins.

An embodiment also provides a method of treating cancer, comprising administering to a patient in need thereof, an effective amount of a compound according to any one of Formulae I-VI, or a pharmaceutically acceptable salt thereof, and an EGFR inhibitor, or a pharmaceutically acceptable salt thereof, in which the cancer has one or more cells that express a mutant KRas G12C protein. An embodiment also provides a compound according to any one of Formulae I-VI, or a pharmaceutically acceptable salt thereof, for use in simultaneous, separate or sequential combination with an EGFR inhibitor, or a pharmaceutically acceptable salt thereof, in the treatment of cancer. An embodiment also provides a combination comprising a compound according to any one of Formulae I-VI, or a pharmaceutically acceptable salt thereof, and an EGFR inhibitor, or a pharmaceutically acceptable salt thereof, for simultaneous, separate, or sequential use in the treatment of cancer. In one embodiment, the compound is a compound of Formulae I-VI or a pharmaceutically acceptable salt thereof. In another embodiment, the EGFR inhibitor is erlotinib. In another embodiment, the EGFR inhibitor is afatinib. In another embodiment, the EGFR inhibitor is gefitinib. In another embodiment, the EGFR inhibitor is cetuximab. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. An embodiment comprises a method of treating KRas G12C mutant bearing cancers of other origins.

An embodiment also provides a method of treating cancer, comprising administering to a patient in need thereof, an effective amount of a compound according to any one of Formulae I-VI, or a pharmaceutically acceptable salt thereof, and an ERK inhibitor, or a pharmaceutically acceptable salt thereof, in which the cancer has one or more cells that express a mutant KRas G12C protein. An embodiment provides a compound according to any one of Formulae I-VI, or a pharmaceutically acceptable salt thereof, for use in simultaneous, separate or sequential combination with an ERK inhibitor, or a pharmaceutically acceptable salt thereof, in the treatment of cancer, in which the cancer has one or more cells that express a mutant KRas G12C protein. An embodiment provides a combination comprising a compound according to any one of Formulae I-VI, or a pharmaceutically acceptable salt thereof, and an ERK inhibitor, or a pharmaceutically acceptable salt thereof, for simultaneous, separate, or sequential use in the treatment of cancer. In one embodiment, the compound is a compound of Formulae I-VI or a pharmaceutically acceptable salt thereof. In another embodiment, the ERK inhibitor is 6,6-dimethyl-2-[2-[(2-methylpyrazol-3-yl)amino]pyrimidin-4-yl]-5-(2-morpholin-4-ylethyl)thieno[2,3-c]pyrrol-4-one. In another embodiment, the ERK inhibitor is LTT462. In another embodiment, the ERK inhibitor is KO-947. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. An embodiment comprises a method of treating KRas G12C mutant bearing cancers of other origins.

An embodiment provides a method of treating cancer, comprising administering to a patient in need thereof, an effective amount of a compound according to any one of Formulae I-VI, or a pharmaceutically acceptable salt thereof, and a platinum agent, in which the cancer has one or more cells that express a mutant KRas G12C protein. An embodiment provides a compound according to any one of Formulae I-VI, or a pharmaceutically acceptable salt thereof, for use in simultaneous, separate or sequential combination with a platinum agent, or a pharmaceutically acceptable salt thereof, in the treatment of cancer, in which the cancer has one or more cells that express a mutant KRas G12C protein. An embodiment provides a combination comprising a compound according to any one of Formulae I-VI, or a pharmaceutically acceptable salt thereof, and a platinum agent, for simultaneous, separate, or sequential use in the treatment of cancer. In one embodiment, the compound is a compound of Formulae I-VI, or a pharmaceutically acceptable salt thereof. In another embodiment, the platinum agent is cisplatin. In another embodiment, the platinum agent is carboplatin. In another embodiment, the platinum agent is oxaliplatin. In another embodiment, the cancer is non-small cell lung carcinoma, in which the cancer has one or more cells that express a KRas G12C mutant protein. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. An embodiment comprises a method of treating KRas G12C mutant bearing cancers of other origins.

An embodiment also provides a method of treating cancer, comprising administering to a patient in need thereof, an effective amount of a compound according to any one of Formulae I-VI, or a pharmaceutically acceptable salt thereof, and pemetrexed, in which the cancer has one or more cells that express a mutant KRas G12C protein. An embodiment provides a compound according to any one of Formulae I-VI, or a pharmaceutically acceptable salt thereof, for use in simultaneous, separate or sequential combination with pemetrexed, in the treatment of cancer, in which the cancer has one or more cells that express a mutant KRas G12C protein. An embodiment also provides a combination comprising a compound according to any one of Formulae I-VI, or a pharmaceutically acceptable salt thereof, and pemetrexed, for simultaneous, separate, or sequential use in the treatment of cancer, in which the cancer has one or more cells that express a mutant KRas G12C protein. In one embodiment, the compound is a compound of Formulae I-VI, or a pharmaceutically acceptable salt thereof. In another embodiment, the cancer is non-small cell lung carcinoma, in which the cancer has one or more cells that express a KRas G12C mutant protein. In another embodiment, a platinum agent is also administered to the patient. In another embodiment, the platinum agent is cisplatin. In another embodiment, the platinum agent is carboplatin. In another embodiment, the platinum agent is oxaliplatin. In another embodiment, the cancer is colorectal carcinoma in which the cancer has one or more cells that express a KRas G12C mutant protein. In another embodiment, the cancer is mutant pancreatic cancer in which the cancer has one or more cells that express a KRas G12C mutant protein. An embodiment comprises a method of treating KRas G12C mutant bearing cancers of other origins.

The term "pharmaceutically acceptable salt" as used herein refers to a salt of a compound considered to be acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences,* 1977, 66(1), 1-19.

The pharmaceutical compositions for the present disclosure may be prepared using pharmaceutically acceptable additives. The term "pharmaceutically acceptable additive(s)" as used herein for the pharmaceutical compositions, refers to one or more carriers, diluents, and excipients that are compatible with the other additives of the composition or formulation and not deleterious to the patient. Examples of pharmaceutical compositions and processes for their preparation can be found in "Remington: The Science and Practice of Pharmacy", Loyd, V., et al. Eds., $22^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose, alginates, gelatin, and polyvinyl-pyrrolidone; kaolin and bentonite; and polyethyl glycols.

As used herein, the term "effective amount" refers to an amount that is a dosage, which is effective in treating a disorder or disease, such as a cancerous lesion or progression of abnormal cell growth and/or cell division. The attending physician, as one skilled in the art, can readily determine an effective amount by the use of conventional techniques and by observing results obtained under analogous circumstances. Dosages per day of treatment normally fall within a range of between about 1 mg per day or twice daily and 1000 mg per day or twice daily, more preferably 100 mg per day or twice daily and 900 mg per day or twice daily. Factors considered in the determination of an effective amount or dose of a compound include: whether the compound or its salt will be administered; the co-administration of other agents, if used; the species of patient to be treated; the patient's size, age, and general health; the degree of involvement or stage and/or the severity of the disorder; the response of the individual patient; the mode of administration; the bioavailability characteristics of the preparation administered; the dose regimen selected; and the use of other concomitant medication.

A treating physician, veterinarian, or other medical person will be able to determine an effective amount of the compound for treatment of a patient in need. Preferred pharmaceutical compositions can be formulated as a tablet or capsule for oral administration, a solution for oral administration, or an injectable solution. The tablet, capsule, or solution can include a compound of the present disclosure in an amount effective for treating a patient in need of treatment for cancer.

As used herein, the terms "treating", "to treat", or "treatment", includes slowing, reducing, stopping, or reversing the progression or severity of an existing symptom, disorder, or condition, which can include specifically slowing the growth of a cancerous lesion or progression of abnormal cell growth and/or cell division.

As used herein, the term "patient" refers to a mammal in need of treatment. Preferably, the patient is a human that is in need of treatment for cancer, for example, KRas G12C mutant bearing cancers.

Certain abbreviations are defined as follows: "ACN" refers to acetonitrile; "Boc-Gly-OH" refers to N-(tert-butoxycarbonyl)glycine; "DCM" refers to dichloromethane; "DIEA" refers to N,N-diisopropyl ethylamine; "DMAP" refers to 4-dimethylaminopyridine; "DMEM" refers to Dulbecco's modified Eagle's medium; "DMF" refers to N,N-dimethyl-formamide; "DMSO" refers to dimethylsulfoxide; "DNA" refers to deoxyribonucleic acid; "DTT" refers to dithiothreitol; "EDTA" refers to ethylenediaminetetraacetic acid; "EGTA" refers to ethylene glycol-bis(β-aminoethyl ether)-N,N,N',N'-tetraacetic acid; "ELISA" refers to enzyme-linked immunosorbent assay; "ERK" refers to extracellular signal-regulated kinases; "EtOAc" refers to ethyl acetate; "EtOH" refers to ethanol; "FBS" refers to fetal bovine serum; "GDP" refers to guanosine diphosphate; "GTP" refers to guanosine triphosphate; "HPLC" refers to high-performance liquid chromatography; "HRP" refers to horseradish peroxidase; "HATU" refers to (1-[bis(dimethylamino)methylene]-1H-1,2,3-triazolo[4,5-b]pyridinium 3-oxide hexafluorophosphate; "IPA" refers to isopropyl alcohol; "IPAm" refers to isopropyl amine; "LC-ES/MS" refers to liquid chromatograph-electrospray mass spectrometry; "LC-MS" refers to liquid chromatography mass spectrometry; "MAPK" refers to mitogen-activated protein kinases; "MeOH" refers to methanol; "NCS" refers to N-chlorosuccinimide; "PCR" refers to polymerase chain reaction; "RPMI" refers to Roswell Park Memorial Institute; "TEA" refers to triethylamine; "TFA" refers to trifluoracetic acid; and "THF" refers to tetrahydrofuran.

Individual isomers, enantiomers, diastereomers, and atropisomers may be separated or resolved at any convenient point in the synthesis of compounds listed below, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The present disclosure includes certain compounds, which are atropisomers and which can exist in different conformations or as different rotomers. Atropisomers are compounds, which exist in different conformations arising from restricted rotation about a single bond. Atropisomers can be isolated as separate chemical species if the energy barrier to rotation about the single is sufficiently high enough and the rate of interconversion is slow enough to allow the individual rotomers to be separated from each other. The present disclosures contemplates all of the isomers, enantiomers, diastereomers, and atropisomers disclosed herein or that could be made using the compounds disclosed herein.

A compound of any one of Formulae I-VI is readily converted to and may be isolated as a pharmaceutically acceptable salt. Salt formation can occur upon the addition of a pharmaceutically acceptable acid to form the acid addition salt. Salts can also form simultaneously upon deprotection of a nitrogen or oxygen, i.e., removing the protecting group. Examples, reactions and conditions for salt formation can be found in Gould, P. L., "Salt selection for basic drugs," *International Journal of Pharmaceutics,* 33: 201-217 (1986); Bastin, R. J., et al. "Salt Selection and Optimization Procedures for Pharmaceutical New Chemical Entities," *Organic Process Research and Development,* 4: 427-435 (2000); and Berge, S. M., et al., "Pharmaceutical Salts," *Journal of Pharmaceutical Sciences,* 66: 1-19, (1977).

The compounds of Formulae I-VI, or salts thereof, may be prepared by a variety of procedures, some of which are illustrated in the Preparations and Examples below. The specific synthetic steps for each of the routes described may be combined in different ways, or in conjunction with steps from different routes, to prepare compounds or salts of the present disclosure. The products of each step in the Preparations below can be recovered by conventional methods, including extraction, evaporation, precipitation, chromatography, filtration, trituration, and crystallization.

PREPARATIONS AND EXAMPLES

The following Preparations and Examples further illustrate the disclosure and represent typical synthesis of the compounds of the disclosure but should not be construed to limit the scope of the disclosure in any way. The reagents and starting materials are readily available or may be readily synthesized either by known procedures or by employing various modifications, which may be made by one of ordinary skill in the art.

Compounds can be characterized by liquid chromatograph-electrospray mass spectrometry (LC-ES/MS) performed on an Agilent HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C-18 2.1×50 mm 3.0 μm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: WATERS™ XTERRA® MS C-18 columns 2.1×50 mm, 3.5 m; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM $NH_4HCO_3$ pH 9; Solvent B: ACN; wavelength: 214 nm.

Preparative reversed phase chromatography is performed on an Agilent 1200 LC-ES/MS equipped with a Mass Selective Detector mass spectrometer and a Leap autosampler/fraction collector. High pH methods are run on a 75×30 mm PHENOMENEX® GEMINI®-NX, 5 μm particle size column with a 10×20 mm guard. Flow rate of 85 mL/min. Eluent is 10 mM ammonium bicarbonate (pH 10) in ACN.

Scheme 1

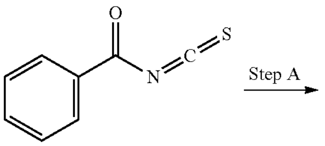

1

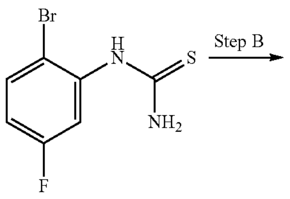

2

-continued

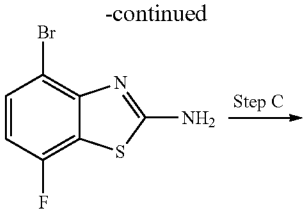

3

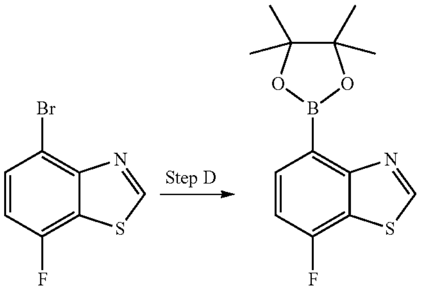

4 5

Scheme 1, step A depicts the thiourea formation from the reaction of compound (1) and 2-bromo-5-fluoroaniline in a solvent such as THF followed by a basic deprotection to afford compound (2). Step B shows the bromination and cyclization of compound (2) using an appropriate brominating agent such as pyridinium tribromide in a solvent such as sulfuric acid to give compound (3). Step C depicts the deamination of compound (3) through treatment with isoamyl nitrite in a suitable solvent such as 1,4-dioxane with heating to give compound (4). Step D shows the conversion of the bromide of compound (4) to a boronic ester through treatment with bis(pinacolato)diboron using a suitable base such as potassium acetate and a catalyst such as [1,1'-bis(diphenylphosphino)ferrocene]dichloropalladium(II) in a solvent such as 1,4-dioxane with heating to give compound (5).

Scheme 2

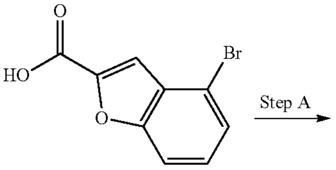

6

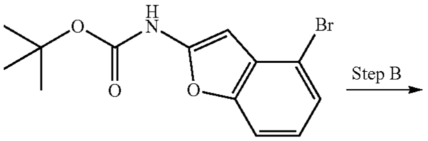

7

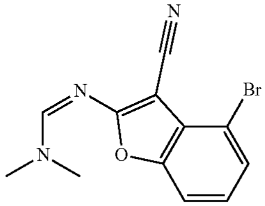

8

Scheme 2, step A depicts the Curtius rearrangement of compound (6) using diphenylphosphoryl azide with a suitable base such as DIEA in a solvent such as tert-butyl alcohol to give compound (7). Step B shows the cyanation of compound (7) with chlorosulfonyl isocyanate in a solvent such as THF followed by treatment with DMF to give compound (8).

Scheme 3

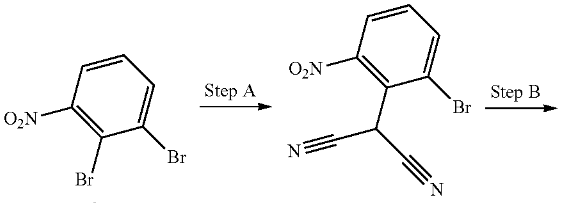

9

10

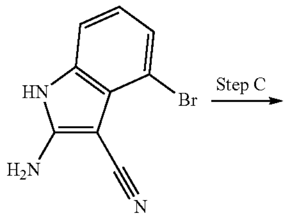

11

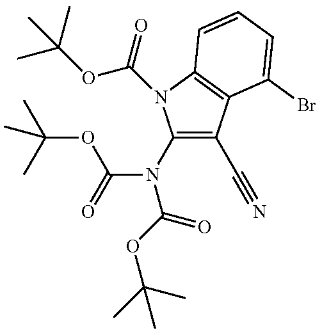

12

Scheme 3, step A depicts the nucleophilic substitution on compound (9) with malononitrile using a suitable base such as NaH in a solvent such as DMF to give compound (10). The reduction of the nitro and subsequent cyclization of compound (10) using zinc and acetic acid to give compound (11) is shown in step B. Step C shows the global protection of compound (11) using di-tert-butyldicarbonate and an appropriate base such as DMAP in a solvent such as THF to give compound (12).

Scheme 4

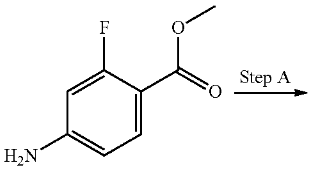

13

-continued

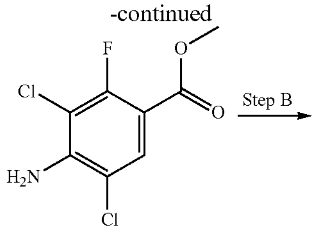

14

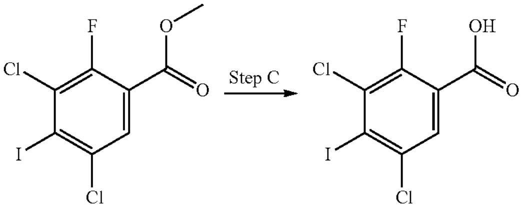

15

16

Scheme 4, step A depicts the chlorination of compound (13) with NCS in an appropriate solvent such as DMF to give compound (14). Step B shows a Sandmeyer reaction to convert the aniline nitrogen of compound (14) to an iodine, the conditions of which will be known by one skilled in the art, to give compound (15). Step C shows the basic hydrolysis of the ester of compound (15) to the acid of compound (16).

Scheme 5

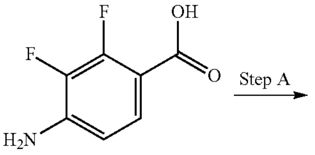

17

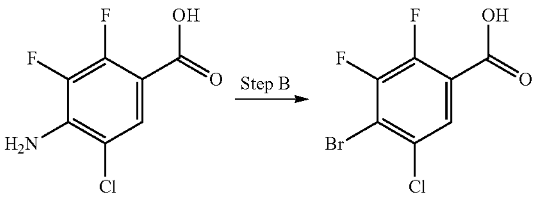

18

19

Scheme 5, step A is performed in a manner essentially analogous to the method in step A of Scheme 4 to give compound (18). Step B shows a Sandmeyer reaction to convert the aniline nitrogen of compound (18) to a bromine to give compound (19), the conditions of which will be known by one skilled in the art.

Scheme 6

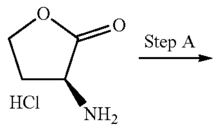

20

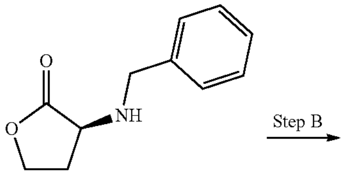

21

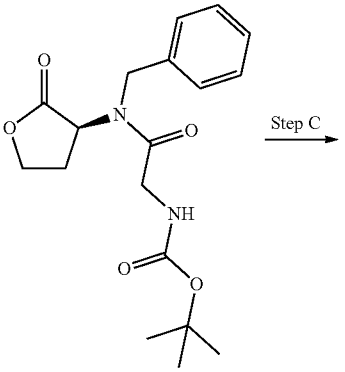

22

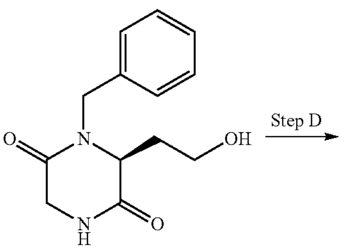

23

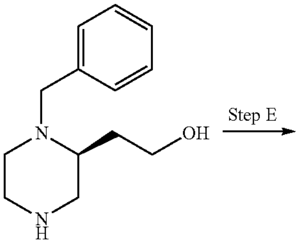

24

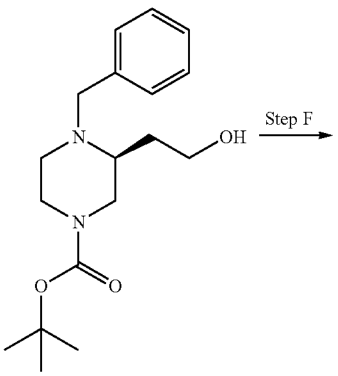

25

-continued

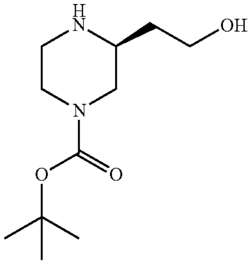

26

Scheme 6, step A depicts a reductive amination between compound (20) and benzaldehyde in a suitable solvent such as DCM with a suitable reducing agent such as sodium triacetoxyborohydride to give compound (21). Step B shows the amide coupling between compound (21) and boc-protected glycine using propylphosphonic anhydride with a suitable base such as TEA in a solvent such as DCM to give compound (22). Step C depicts the acidic deprotection and rearrangement of compound (22) using TFA in a solvent such as DCM to give compound (23). Step D shows the global amide reduction of compound (23) using a reducing agent such as lithium aluminum hydride in a solvent such as THF to give compound (24). Step E depicts the protection of compound (24) using di-tert-butyl dicarbonate in aqueous sodium bicarbonate to give compound (25). Step F shows the deprotection of compound (25) by means of hydrogenation to give compound (26).

Scheme 7

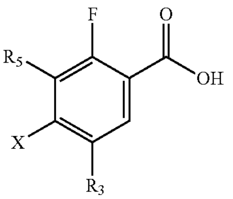

+

27

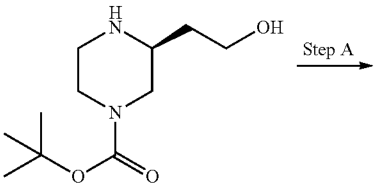

26

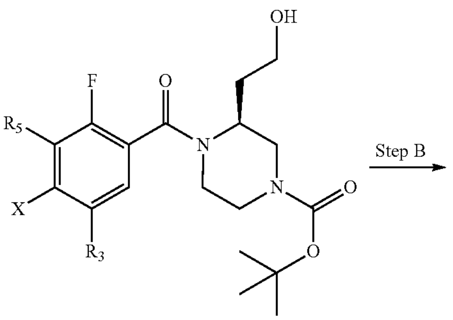

28

-continued

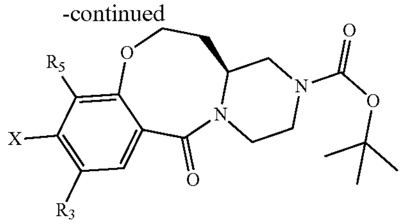

29

-continued

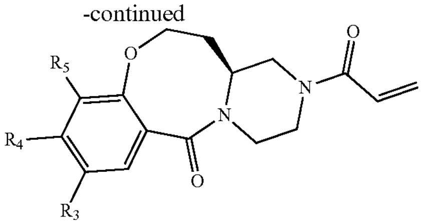

33

In Scheme 7, compound (27) represents benzoic acids from Schemes 4-5 as well as commercially available benzoic acids. The amide coupling between compound (27) and compound (26) using HATU and an appropriate base such as DIEA in a solvent such as THF to give compound (28) is shown in step A. One skilled in the art will recognize that there are a variety of conditions with which to perform an amide coupling. Step B depicts the intramolecular cyclization of compound (28) to compound (29) using an appropriate base such as sodium hydride in a solvent such as DMF.

Scheme 8

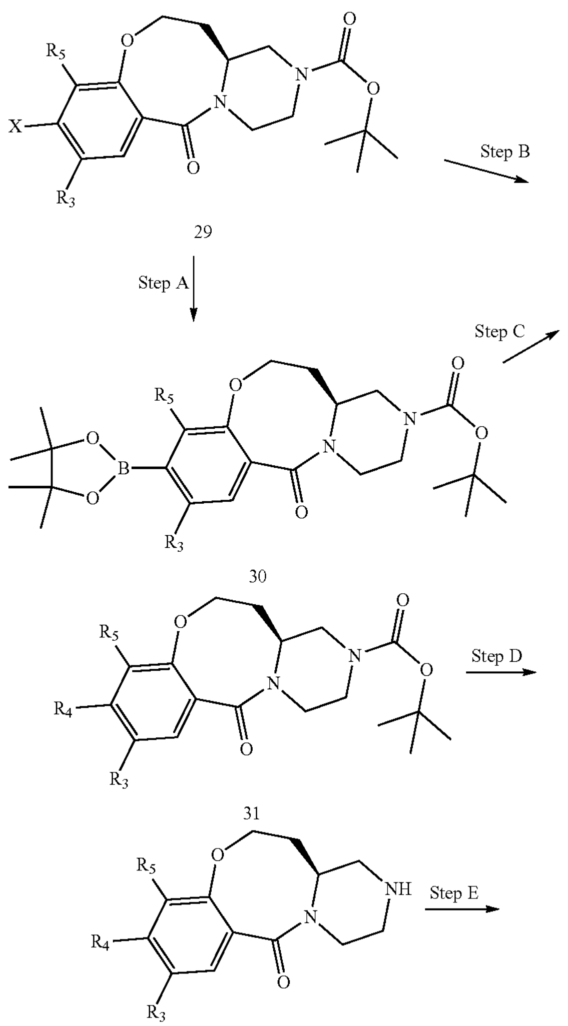

29

30

31

32

Scheme 8, step A is performed in a manner essentially analogous to the method in step D of Scheme 1 to give compound (30). Step B depicts a Suzuki cross-coupling between compound (29) and an appropriate boronate using a suitable catalyst such as [1,1'-bis(diphenylphosphino) ferrocene]dichloropalladium (II) with a suitable base such as potassium phosphate tribasic in a solvent system such as 1,4-dioxane and water with heating to give compound (31). Step C also leads to compound (31) through a Suzuki cross-coupling between compound (30) and an appropriate coupling partner using a suitable catalyst such as 1,1'-bis (di-tert-butylphosphino) ferrocene palladium dichloride with a suitable base such as potassium carbonate in a solvent system such as 1,4-dioxane and water with heating. Step D shows the acidic deprotection of compound (31) with an acid such as TFA in a solvent such as DCM to give compound (32). Step E shows the amide formation between compound (32) and acryloyl chloride using a suitable base such as DIEA in a solvent such as DCM to give compound (33). This amide can also be formed using potassium carbonate as the base in a biphasic solvent system such as EtOAc, THF, and water.

Preparation 1 tert-Butyl N-(4-bromo-1,3-benzoxazol-2-yl)carbamate

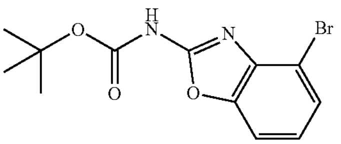 [SMILES: CC(C)(C)OC(=O)Nc1nc2c(Br)cccc2o1]

Di-tert-butyl dicarbonate (724 mg, 3.317 mmol) and DMAP (28 mg, 0.227 mmol) are added to a mixture of 4-bromobenzo[d]oxazol-2-amine (504 mg, 2.248 mmol) in DCM (11 ml). The resulting mixture is stirred for 18 hours under nitrogen at ambient temperature. After this time additional di-tert-butyl dicarbonate (490 mg, 2.245 mmol) is added to the mixture and stirred for 1 hour at ambient temperature before adding sodium methoxide (5M in MeOH) (4.5 mL, 23 mmol) and stirring vigorously for 10 minutes. The mixture is diluted with DCM and water. The aqueous layer is adjusted to pH 9 with saturated ammonium chloride solution and the layers are separated. The aqueous is extracted twice more with DCM. The organics are combined, passed through a hydrophobic frit, and concentrated in vacuo. The resulting residue is purified by silica gel flash chromatography, eluting with 5-25% acetone/hexane to give the title compound as a white solid (638 mg, 91%). ES/MS m/z ($^{79}$Br/$^{81}$Br) 256.8/258.8 [M-t-Bu+H]$^+$.

Preparation 2

N-[(2-Bromo-5-fluoro-phenyl)carbamothioyl]benzamide

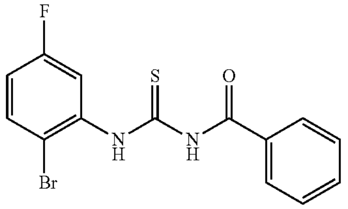 [SMILES: O=C(NC(=S)Nc1cc(F)ccc1Br)c1ccccc1]

A solution of 2-bromo-5-fluoroaniline (250 g, 1289.4 mmol) in THF (400 mL) is stirred with an overhead mechanical stirrer. Benzoyl isothiocyanate (130 g, 780.6 mmol) in THF (800 mL) is added over 30 minutes using an addition funnel. A water bath is used to keep internal temperature below 30° C. during the addition. After 1.5 hours, the reaction mixture is poured equally into three 4-liter flasks containing water (3 L). The resulting solids are vacuum filtered through a sintered glass funnel. The solids are rinsed with deionized water (8 L) and air dried under vacuum to give the title compound as a tan colored solid (456 g, 99+%). ES/MS m/z ($^{79}$Br/$^{81}$Br) 353/355 [M−H]$^-$.

Preparation 3

(2-Bromo-5-fluoro-phenyl)thiourea

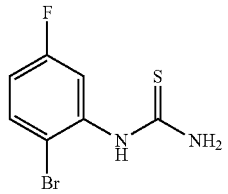 [SMILES: NC(=S)Nc1cc(F)ccc1Br]

To a suspension of N-[(2-bromo-5-fluoro-phenyl)carbamothioyl]benzamide (1600 g, 4.53 mol), THF (6 L), and MeOH (1.6 L) is added aqueous 5N NaOH (1 L). After 18 hours of stirring at ambient temperature, the reaction mixture is filtered through a pad of diatomaceous earth to remove black particulates. The pad is rinsed with THF/MeOH then 100% MeOH. The solvent is removed in vacuo to obtain a tan solid. Ice water (4 L) is added to the solid and with the use of an overhead stirrer, 5N HCl (300 mL) is added in 100 mL portions to adjust the pH to 7. Additional ice water is added, and the mixture is stirred for 1 hour. Water (4 L) is added and the suspension is filtered through a large sintered glass funnel under vacuum. The solids are rinsed with deionized water and after most of the water is removed, the solids are rinsed with hexanes (8 L), and air dried. The solids are placed in a vacuum oven at 50° C. for 24 hours to give the title compound as an off-white solid (1035 g, 92%). ES/MS m/z ($^{79}$Br/$^{81}$Br) 249/251 [M−H]$^-$ Preparation 4

4-Bromo-7-fluoro-1,3-benzothiazol-2-amine

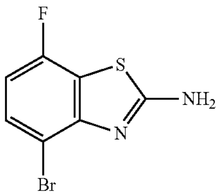 [SMILES: Nc1nc2c(Br)ccc(F)c2s1]

Sulfuric acid (350 mL), cooled with an ice/sodium chloride bath, is stirred with an overhead mechanical stirrer. (2-Bromo-5-fluoro-phenyl)thiourea (130.5 g, 523.9 mmol) is added in portions over a five minute period. After ten minutes, the internal temperature reached 1° C. Under nitrogen, pyridinium tribromide (185 g, 549.53 mmol) is added in 8 portions over a period of 15 minutes while maintaining the internal temperature below 5° C. The vapor generated is bubbled through a NaOH trap cooled in ice. After stirring at 0° C. for 75 minutes, the reaction is warmed to ambient temperature. The reaction is then heated to an initial internal temperature of 50° C. then gradually heated to 59° C. After 1.5 hours, the reaction is cooled to ambient temperature. The reaction mixture is poured into a large flask containing ice. The pH is carefully adjusted to 7 with 18.9N NaOH (620 mL). The solids are filtered through a sintered glass funnel and rinsed with deionized water until the filtrate pH matched that of deionized water. The solid is air dried then placed in a vacuum oven at 50° C. for 24 hours to give the title compound as a tan solid (129.3 g, 99+%). ES/MS m/z ($^{79}$Br/$^{81}$Br) 247/249 [M+H]$^+$.

Preparation 5

4-Bromo-7-fluoro-1,3-benzothiazole

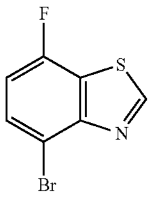 [SMILES: Fc1ccc(Br)c2ncsc12]

A solution of 4-bromo-7-fluoro-1,3-benzothiazol-2-amine (626 mg, 2.53 mmol), 1,4-dioxane (10 mL), and isoamyl nitrite (0.50 mL, 3.7 mmol) is stirred at 60° C. for 1 hour. Once cooled, the reaction mixture is concentrated in vacuo. The crude material is purified by silica gel flash chromatography eluting with 5-20% EtOAc/hexane to give the title compound (359 mg, 99+%). $^1$H NMR (DMSO-d6) δ 9.59 (1H, s), 7.87 (1H, dd, J=7.9, 7.41 (1H, t, J=8.8 Hz).

Preparation 6 tert-Butyl N-(4-bromobenzofuran-2-yl)carbamate

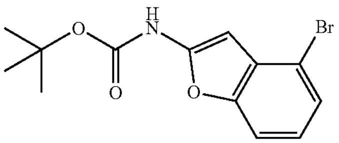 [SMILES: CC(C)(C)OC(=O)Nc1cc2c(Br)cccc2o1]

A mixture of 4-bromobenzofuran-2-carboxylic acid (1.00 g, 4.15 mmol), diphenylphosphoryl azide (1.34 mL, 6.20 mmol), and DIEA (1.09 mL, 6.25 mmol) in tert-butyl alcohol (12 mL) is stirred for 10 minutes at ambient temperature before heating to 95° C. After 2.5 hours, the heat is removed and the solvents are removed in vacuo. The resulting residue is purified via silica gel flash chromatography eluting with 0-50% EtOAc/hexane to give the title compound as a white solid (850 mg, 66%). ES/MS m/z ($^{79}Br/^{81}Br$) 255.6/257.6 $[M\text{-}t\text{-}Bu+H]^+$ Preparation 7

N'-(4-Bromo-3-cyano-benzofuran-2-yl)-N,N-dimethyl-formamidine

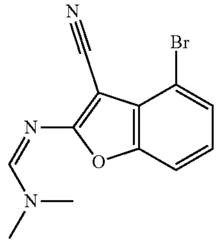 [SMILES: CN(C)/C=N\c1oc2cccc(Br)c2c1C#N]

To a −78° C. stirring mixture of tert-butyl N-(4-bromobenzofuran-2-yl)carbamate (500 mg, 1.60 mmol) in THF (8 mL) is added chlorosulfonyl isocyanate (0.21 mL, 2.40 mmol). After one hour, chlorosulfonyl isocyanate (0.21 mL, 2.40 mmol) is added again and stirred at −78° C. for an additional hour. After this time, the mixture is poured into DMF (5 mL) and stirred at ambient temperature for 20 minutes. The mixture is then diluted with EtOAc and washed twice with saturated aqueous sodium bicarbonate solution and once with saturated aqueous sodium chloride solution. The organics are dried over sodium sulfate, filtered, and concentrated in vacuo. The resulting residue is purified via silica gel flash chromatography eluting with 0-100% EtOAc/hexane to give the title compound as a light yellow solid (210 mg, 37%). ES/MS m/z ($^{79}Br/^{81}Br$) 291.6/293.6 $[M+H]^+$.

Preparation 8

1-Iodo-7-nitro-naphthalene

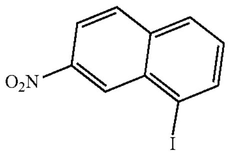 [SMILES: O=[N+]([O-])c1ccc2cccc(I)c2c1]

A suspension of 7-nitronaphthalen-1-amine (1.15 g, 6.11 mmol), tert-butylnitrite (3.2 mL, 24 mmol) and cuprous iodide (2.39 g, 12.3 mmol) in ACN (12 mL) is stirred at 50° C. for two hours. The mixture is concentrated in vacuo, diluted with EtOAc, and washed successively with 1N HCl, saturated $NaHSO_3$ solution, and saturated aqueous sodium chloride solution. The organics are dried over anhydrous sodium sulfate, filtered, and concentrated in vacuo. The resulting residue is purified via silica gel flash chromatography eluting with 0-10% acetone/heptane to give the title compound as a light yellow solid (745 mg, 41%). EI/MS m/z 299 [M].

Preparation 9

2-(2-Bromo-6-nitro-phenyl)propanedinitrile

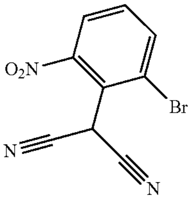 [SMILES: N#CC(C#N)c1c(Br)cccc1[N+](=O)[O-]]

To a 0° C. solution of malononitrile (0.911 g, 13.8 mmol) in DMF (15 mL) is added sodium hydride (60% suspension in mineral oil, 0.32 g, 8.0 mmol). The mixture is stirred for 30 minutes. Solid 1,2-dibromo-3-nitrobenzene (2.0 g, 6.8 mmol) is added in several portions and the mixture heated at 70° C. After five hours, the mixture is cooled to ambient temperature, diluted with water, and the pH adjusted to 2 with concentrated HCl. The aqueous solution is extracted with EtOAc and the combined organics are washed with 0.2M aqueous LiCl solution, dried over anhydrous sodium sulfate, and concentrated in vacuo. The resulting solids were used in the next step as crude (2.9 g, 99+%). ES/MS m/z ($^{79}Br/^{81}Br$) 264/266 $[M-H]^-$.

Preparation 10

2-Amino-4-bromo-1H-indole-3-carbonitrile

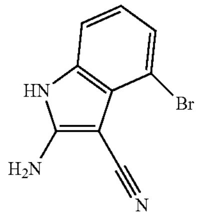 [SMILES: N#Cc1c(N)[nH]c2cccc(Br)c12]

Crude 2-(2-bromo-6-nitro-phenyl)propanedinitrile (2.9 g) and zinc powder (9.0 g, 117 mmol) are suspended in glacial acetic acid (70 mL) and heated at 75° C. After one hour, the mixture is cooled to ambient temperature and concentrated in vacuo, then diluted with EtOAc and washed with saturated sodium bicarbonate solution. The organics are dried over anhydrous sodium sulfate, filtered, and concentrated in vacuo. The resulting residue is purified via silica gel flash chromatography eluting with 0-50% acetone/hexanes to give the title compound as a tan solid (550 mg, 32%). ES/MS m/z ($^{79}Br/^{81}Br$) 236/238 $[M+H]^+$.

Preparation 11 tert-Butyl 2-[bis(tert-butoxycarbonyl)amino]-4-bromo-3-cyano-indole-1-carboxylate

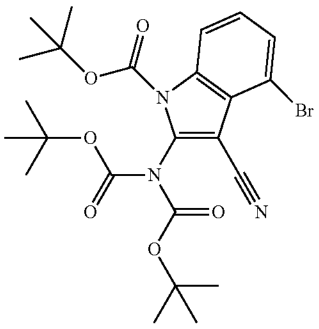 [SMILES: CC(C)(C)OC(=O)N(C(=O)OC(C)(C)C)c1c(C#N)c2c(Br)cccc2n1C(=O)OC(C)(C)C]

A solution of 2-amino-4-bromo-1H-indole-3-carbonitrile (0.320 g, 1.36 mmol) in THF (7 mL) is treated with DMAP (0.033 g, 0.27 mmol) and di-tert-butyldicarbonate (1.26 g, 5.60 mmol) and stirred at room temperature for 22 hours. The mixture is diluted with EtOAc and washed with saturated ammonium chloride solution and saturated aqueous sodium chloride solution, dried over anhydrous sodium sulfate, and concentrated in vacuo. The resulting residue is purified via silica gel flash chromatography eluting with 0-30% EtOAc/hexanes to give the title compound as a white solid (327 mg, 45%). ES/MS m/z ($^{79}Br/^{81}Br$) 434/436 $[M-Boc-H]^-$.

Preparation 12

2-(7-Fluorobenzothiophen-4-yl)-4,4,5,5-tetramethyl-1,3,2-dioxaborolane

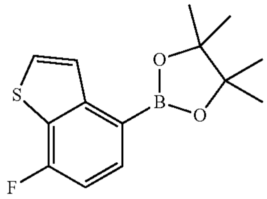 [SMILES: CC1(C)OB(c2ccc(F)c3sccc23)OC1(C)C]

7-Fluorobenzothiophen-4-ol (200 mg, 1.19 mmol) is dissolved in DCM (12 mL) and pyridine (0.2 mL, 2 mmol) is added. The mixture is cooled to 0° C. and trifluoromethanesulfonic anhydride (0.24 mL, 1.4 mmol) is added dropwise. The solution is stirred at 0° C. for 1 hour. The reaction mixture is quenched with saturated aqueous sodium bicarbonate solution (5 mL) and diluted with EtOAc (70 mL). The organic layer is separated, washed with saturated aqueous sodium chloride solution (30 mL), dried over sodium sulfate, filtered, and concentrated in vacuo. The resulting residue is immediately suspended in 1,4-dioxane (8 mL) and bis(pinacolato) diboron (453 mg, 1.78 mmol), 1,1'-bis(diphenylphosphino)ferrocene-palladium(II) dichloride DCM complex (100 mg, 0.120 mmol), and potassium acetate (350 mg, 3.57 mmol) are added sequentially. The mixture is sparged with nitrogen for 10 minutes and then heated to 110° C. with stirring. After stirring for 1 hour, the mixture is cooled and diluted with EtOAc (150 mL). The organic layer is washed with saturated aqueous sodium chloride solution (100 mL), dried over sodium sulfate, filtered, and concentrated in vacuo. The resulting residue is purified via silica gel flash chromatography eluting with 10% EtOAc/hexanes to give the title compound as a white solid (76.1 mg, 23%). $^1H$ NMR ($CDCl_3$) δ 8.03 (1H, dd, J=5.5, 4.0 Hz), 7.87 (1H, dd, J=7.9, 5.7 Hz), 7.52 (1H, d, J=5.4 Hz), 7.04 (1H, dd, J=9.9, 7.9 Hz), 1.38 (s, 12H).

Preparation 13

4-(4,4,5,5-Tetramethyl-1,3,2-dioxaborolan-2-yl)-1,3-benzothiazole

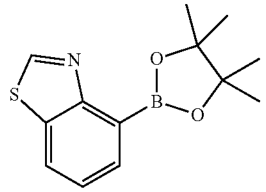 [SMILES: CC1(C)OB(c2cccc3scnc23)OC1(C)C]

Potassium acetate (500 mg, 5.09 mmol), 4-bromo-1,3-benzothiazole (365 mg, 1.70 mmol), and bis(pinacolato) diboron (662 mg, 2.61 mmol) are added to a vial. 1,4-Dioxane (11 mL) is added under nitrogen and the mixture is purged with nitrogen for 10 minutes. [1,1'-Bis(diphenylphosphino)ferrocene]dichloropalladium(II) (134 mg, 0.18 mmol) is added in one portion and the vial is sealed. The mixture is stirred at 110° C. for one hour and then at 80° C. for 18 hours. The reaction mixture is cooled to ambient temperature and filtered through a pad of diatomaceous earth. The filtrate is concentrated in vacuo and purified via silica gel flash chromatography eluting with 0-100% EtOAc/hexanes to give the title compound (386 mg, 56%). $^1H$ NMR (DMSO-d6) δ 9.43 (1H, s), 8.30 (dd, J=8.0, 1.0 Hz, 1H), 7.83 (dd, J=7.0, 1.0 Hz, 1H), 7.48 (t, J=7.5 Hz, 1H), 1.34 (s, 12H).

TABLE 1

Compounds made in a manner essentially analogous to the method of Preparation 13.

| Preparation | Structure | Compound Name | ES/MS m/z (M + H) |
|---|---|---|---|
| 14 | 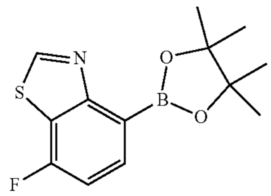 [SMILES: CC1(C)OB(c2ccc(F)c3scnc23)OC1(C)C] | 7-Fluoro-4-(4,4,5,5-tetramethyl-1,3,2-dioxaborolan-2-yl)-1,3-benzothiazole | 280.2 |
| 15 | 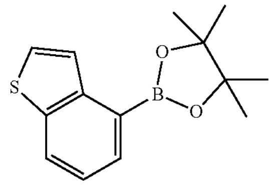 [SMILES: CC1(C)OB(c2cccc3sccc23)OC1(C)C] | 2-(Benzothiophen-4-yl)-4,4,5,5-tetramethyl-1,3,2-dioxaborolane | See 1H NMR data below |

NMR data for intermediate 15: $^1$H NMR (DMSO-d6) δ 8.15 (1H, d, J=8.1 Hz), 7.89 (1H, d, J=5.3 Hz), 7.83 (1H, d, J=5.7 Hz), 7.76 (1H, dd, J=6.9, 1.0 Hz), 1.35 (12H, s).

Preparation 16

Methyl 4-amino-3,5-dichloro-2-fluoro-benzoate

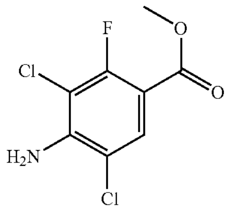

Methyl 4-amino-2-fluoro-benzoate (27.0 g, 160 mmol) and NCS (46.3 g, 336 mmol) are dissolved in DMF (300 mL) and heated at 80° C. After 40 minutes, the reaction mixture is poured over ice water and extracted twice with EtOAc. The combined organic extracts are washed once with 5N NaOH, twice with 0.2N LiCl, dried over anhydrous magnesium sulfate, filtered, and concentrated in vacuo to give the title compound (37.0 g, 97%). ES/MS m/z ($^{35}$Cl/$^{37}$Cl) 238/240 [M+H]$^+$.

TABLE 2

Compound made in a manner essentially analogous to the method of Preparation 16.

| Preparation | Structure | Compound Name | NMR |
|---|---|---|---|
| 17 | 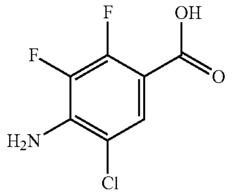 [SMILES: Nc1c(Cl)cc(C(=O)O)c(F)c1F] | 4-Amino-5-chloro-2,3-difluoro-benzoic acid | $^1$H NMR (DMSO-d6) δ 12.96 (s, 1H), 7.54 (dd, J = 2.1, 6.9 Hz, 1H), 6.56 (bs, 2H) |

Preparation 18

3,5-Dichloro-2-fluoro-4-iodo-benzoic Acid

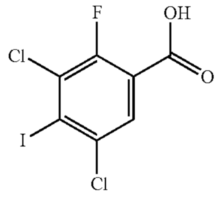 [SMILES: O=C(O)c1cc(Cl)c(I)c(Cl)c1F]

Cuprous iodide (10.0 g, 51.5 mmol), ACN (128 mL) and tert-butyl nitrite (13.6 mL, 103 mmol) are combined and the mixture is heated at 50° C. for 30 minutes and then to the mixture is added methyl 4-amino-3,5-dichloro-2-fluoro-benzoate (6.11 g, 25.7 mmol). Gas evolution is noted. After 1 hour 40 minutes at 50° C. the solvent is removed in vacuo. Water, EtOAc, and 1N HCl are added. The aqueous layer is extracted twice with EtOAc. The combined organic extracts are washed with aqueous sodium bisulfite, dried over anhydrous magnesium sulfate, filtered, and concentrated in vacuo. The crude mixture is purified by silica gel flash chromatography eluting with 3-5% EtOAc in hexanes. The cleanest fractions are combined and concentrated in vacuo to give the methyl ester intermediate (5.85 g, 65%).

To methyl 3,5-dichloro-2-fluoro-4-iodo-benzoate (5.85 g, 16.8 mmol) is added MeOH (170 mL) and 1N NaOH (17 mL). In the course of stirring at ambient temperature over 40 minutes, the material is fully dissolved. The MeOH is removed in vacuo. To the residue is added EtOAc and 1N HCl. The aqueous layer is extracted twice with EtOAc and the combined organic extracts are dried over anhydrous magnesium sulfate, filtered, and concentrated in vacuo to give the title compound (5.56 g, 99%): $^1$H NMR ($CDCl_3$) δ 8.063-8.08 (d, 1H, J=6.34 Hz).

Preparation 19

4-Bromo-5-chloro-2,3-difluoro-benzoic Acid

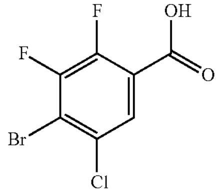

A solution of 4-amino-2,3-difluoro-benzoic acid (33.3 g, 192 mmol) in ACN (400 mL) is added to a 3-neck flask equipped with a reflux condenser. NCS (34.5 g, 251 mmol) is added in small portions. The mixture is then heated to 80° C. and stirred for 2.5 hours. After this time, the reaction is cooled to ambient temperature and then to 10° C. in an ice-water bath. Water (1.2 L) is added dropwise and stirring is continued for 1 hour. The mixture is then stirred while warming to ambient temperature for 3 days. The resulting solid is then collected by filtration to obtain 4-amino-5-chloro-2,3-difluoro-benzoic acid (39.9 g, 65%). $^1$H NMR (DMSO-d6) δ 12.96 (s, 1H), 7.54 (dd, J=6.9, 2.1 Hz, 1H).

A solution of cupric bromide (2.15 g, 9.63 mmol) and tert-butyl nitrite (2.55 mL, 19.3 mmol) in ACN (25 mL) is added to a flask and the vessel is placed in an oil bath preheated to 80° C. 4-Amino-5-chloro-2,3-difluoro-benzoic acid (1.00 g, 4.82 mmol) is added portionwise and stirring is continued at 80° C. After 1.5 hours, the mixture is cooled to ambient temperature and concentrated in vacuo. The mixture is diluted with EtOAc (50 mL) and washed with 1N HCl (2×50 mL) and saturated aqueous $NaHSO_3$ (50 mL). The organic layer is dried over sodium sulfate, filtered, and concentrated in vacuo to give the title compound (1.30 g, 82%). $^1$H NMR (DMSO-d6) δ 7.89 (dd, J=2.2, 6.2 Hz, 1H).

Preparation 20

(3S)-3-(Benzylamino)tetrahydrofuran-2-one

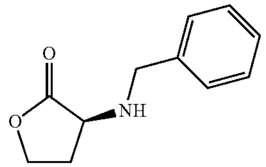 [SMILES: O=C1OCC[C@@H]1NCc1ccccc1]

A suspension L-homoserine lactone hydrochloride (100 g, 726.93 mmol, 4 Å powdered molecular sieves (178 g), and benzaldehyde (57 mL, 561.3 mmol) in DCM (2500 mL) is stirred overnight under nitrogen at 35° C. After this time, the heating is removed and the mixture is cooled to 20° C. Sodium triacetoxyborohydride (208 g, 981.41 mmol) is added to the mixture which after 20 minutes is then allowed to warm to ambient temperature and stirred for 2 hours. After this time, the mixture is cooled to −10° C. and carefully quenched with saturated aqueous sodium bicarbonate solution (400 mL). The pH is adjusted to 8 with saturated aqueous sodium bicarbonate solution and solid sodium bicarbonate. The mixture is filtered through a pad of diatomaceous earth and rinsed through with DCM. The layers are separated and the aqueous is extracted an additional time with DCM (1 L). The combined organics are dried over sodium sulfate, filtered, and concentrated in vacuo to give the title compound as a clear oil (87 g, 66.5%, 81 mass %). ES/MS m/z: 192.2 (M+H). For further analytical work, a sample of the title compound (1 g) is purified by silica gel flash chromatography eluting with 10-50% EtOAc/DCM to give 422 mg of purified title compound. This material is analyzed using Chiralpak® IC, 4.6×150 mm, 10% IPA (0.2% IPAm)/$CO_2$, 5 mL/min, 225 nm showing >98% e.e.

Preparation 21 tert-Butyl N-[2-[benzyl-[(3S)-2-oxotetrahydrofuran-3-yl]amino]-2-oxo-ethyl]carbamate

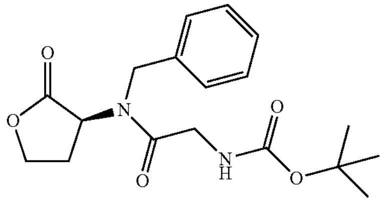 [SMILES: CC(C)(C)OC(=O)NCC(=O)N(Cc1ccccc1)[C@H]1CCOC1=O]

A mixture of (3S)-3-(benzylamino)tetrahydrofuran-2-one (86 g, 364.27 mmol, 81 mass %), boc-Gly-OH (97 g, 553.71 mmol), and TEA (103 mL, 739 mmol) in DCM (700 mL) is cooled to 5° C. Propylphosphonic anhydride (50 mass % in EtOAc) (430 mL, 737 mmol) is added dropwise over one hour to the mixture while keeping the internal temperature around 10° C. Upon addition, the mixture is allowed to warm to ambient temperature. After seven hours, the mixture is cooled to 10° C. and additional boc-Gly-OH (3.1 g, 18 mmol), TEA (5 mL, 35.9 mmol), and propylphosphonic anhydride (50 mass % in EtOAc) (22 mL, 37.7 mmol) are added. The mixture is warmed to ambient temperature and stirred overnight. After this time, the mixture is cooled to 8° C. and additional boc-Gly-OH (9.6 g, 55 mmol), TEA (10 mL, 71.7 mmol), and propylphosphonic anhydride (50 mass % in EtOAc) (42 mL, 71.9 mmol) are added. The mixture is warmed to ambient temperature and stirred for seven hours. After this time, the mixture is poured over ice and quenched carefully with saturated aqueous sodium bicarbonate solution (1 L). The pH is adjusted to 8 with solid sodium bicarbonate and the layers are separated. The aqueous is extracted twice more with DCM. The combined organics are washed with saturated aqueous sodium chloride solution (500 mL). The organic layer is filtered through a pad of diatomaceous earth and sodium sulfate. The organics are concentrated in vacuo to a volume of 1 L and washed twice with saturated aqueous sodium chloride solution. The organics are dried over magnesium sulfate, filtered, and concentrated in vacuo to give the title compound to be used without further purification (194 g, 53.5%, 35 mass %). ES/MS m/z: 249.0 (M-t-Bu+H)

Preparation 22

(6S)-1-Benzyl-6-(2-hydroxyethyl)piperazine-2,5-dione

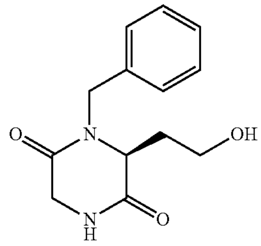 [SMILES: O=C1NCC(=O)N(Cc2ccccc2)[C@H]1CCO]

TFA (100 mL, 1310 mmol) is added to a mixture of tert-butyl N-[2-[benzyl-[(3S)-2-oxotetrahydrofuran-3-yl]amino]-2-oxo-ethyl]carbamate (194 g, 194.9 mmol, 35 mass %) in DCM (500 mL). The mixture is stirred at ambient temperature overnight. After this time, additional TFA (50 mL, 653 mmol) is added and the mixture is stirred at ambient temperature. After two hours, additional TFA (50 mL, 653 mmol) is added and the mixture is stirred at ambient temperature overnight. After this time, the mixture is concentrated in vacuo. The resulting residue is diluted with water (600 mL) and washed twice with diethyl ether. The pH is adjusted to 7 with 1N NaOH and further adjusted to pH 12 with 5N NaOH. MeOH (10 mL) is added and the mixture is stirred at ambient temperature. Additional 5N NaOH is added to the mixture at five minute intervals to readjust the pH to 12. Overall, the mixture is stirred at pH 12 for 35 minutes. After this time, the pH is adjusted to 8 with 10% aqueous HCl solution and extracted with DCM (5×1 L). The aqueous pH is then adjusted to 5 with 10% aqueous HCl solution and again extracted with DCM (1 L). The combined organics are dried over sodium sulfate, filtered, and concentrated in vacuo to give the title compound as a light tan solid (17 g, 33.4%). Additional extractions of the aqueous are performed with alternating 25% IPA/chloroform and DCM until the title product is removed from the aqueous according to LC/MS. To the combined organics is added IPA (150 mL). The organics are washed with saturated aqueous sodium chloride solution twice, dried over sodium sulfate and magnesium sulfate, filtered, and concentrated in vacuo to give additional title compound (17.2 g, 35.5%) for an overall yield of 34.2 g (68.9%). ES/MS m/z: 249.0 (M+H).

Preparation 23

2-[(2S)-1-Benzylpiperazin-2-yl]ethanol

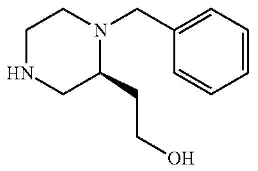 [SMILES: OCC[C@H]1CNCCN1Cc1ccccc1]

To a 45° C. solution of 2M lithium aluminum hydride in THF (131 mL, 262 mmol) is added a solution of (6S)-1-benzyl-6-(2-hydroxyethyl)piperazine-2,5-dione (34 g, 131.5 mmol) in THF (200 mL) in a dropwise fashion. After addition, the mixture is heated to 60° C. After 3.5 hours, additional 2M lithium aluminum hydride in THF (33 mL, 66 mmol) is added and the mixture is stirred at 60° C. After an hour, additional 2M lithium aluminum hydride in THF (131 mL, 262 mmol) is added and the mixture is stirred at 60° C. overnight. After this time, 2M lithium aluminum hydride in THF (6 mL, 12 mmol) is added and the mixture is stirred at 60° C. After four hours, 2M lithium aluminum hydride in THF (6 mL, 12 mmol) is added and the mixture is stirred for two hours at 60° C. The heat is removed and the mixture is cooled to 10° C. Water (16 mL) is added dropwise, followed by dropwise addition of 3.75M aqueous NaOH (16 mL) then THF (300 mL). Water (48 mL) is added and the resulting mixture is stirred overnight at ambient temperature. After this time, the mixture is filtered through a pad of diatomaceous earth and rinsed through with EtOAc. The filtrate is concentrated in vacuo to give the title product (28.8 g, 67.6%, 68 mass %). ES/MS m/z: 221.0 (M+H).

Preparation 24 tert-Butyl (3S)-4-benzyl-3-(2-hydroxyethyl)piperazine-1-carboxylate

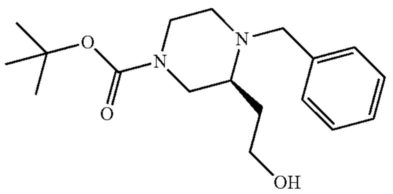 [SMILES: CC(C)(C)OC(=O)N1CCN(Cc2ccccc2)[C@@H](CCO)C1]

Sodium bicarbonate (80 g, 952 mmol) in water (500 mL) is added to 2-[(2S)-1-benzylpiperazin-2-yl]ethanol (28 g, 86.43 mmol) in 1,4-dioxane (500 mL) at ambient temperature. Di-tert-butyl dicarbonate (26.6 g, 122 mmol) is added and the mixture is stirred at ambient temperature for 20 minutes. After this time, ice (400 mL), water (200 mL), and EtOAc (1 L) are added and the layers separated. The aqueous is extracted once more with EtOAc (1 L). The combined organics are washed with water (250 mL) and saturated aqueous sodium chloride solution (250 mL), dried over sodium sulfate, filtered, and concentrated in vacuo. The resulting oil is purified by silica gel flash chromatography eluting with 10-70% EtOAc/hexanes to give the title compound (20.79 g, 74%). ES/MS m/z: 321.2 (M+H). The material is analyzed using Chiralpak® IC, 4.6×150 mm, 15% IPA (0.2% IPAm)/$CO_2$, 5 mL/min, 225 nm showing 96% e.e.

Preparation 25 tert-Butyl (3S)-3-(2-hydroxyethyl)piperazine-1-carboxylate

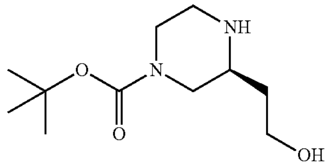 [SMILES: CC(C)(C)OC(=O)N1CCN[C@@H](CCO)C1]

20% $Pd(OH)_2$ on carbon (24.39 g, 176.4 mmol) is added to a vessel which is purged with nitrogen. EtOH (620 mL) is added to the vessel followed by tert-butyl (3S)-4-benzyl-3-(2-hydroxyethyl)piperazine-1-carboxylate (61.93 g, 193.3 mmol) and EtOH (620 mL). The vessel is sealed, purged with nitrogen, purged with hydrogen, and pressurized under hydrogen (60 psi). The vessel is placed on a Parr shaker for 15 hours at ambient temperature. After this time, the reaction mixture is filtered and concentrated in vacuo to give the title compound (42.74 g, 98%). ES/MS m/z 231.0: (M+H).

Preparation 26 tert-Butyl (3S)-4-(3,5-dichloro-2-fluoro-4-iodo-benzoyl)-3-(2-hydroxyethyl)piperazine-1-carboxylate

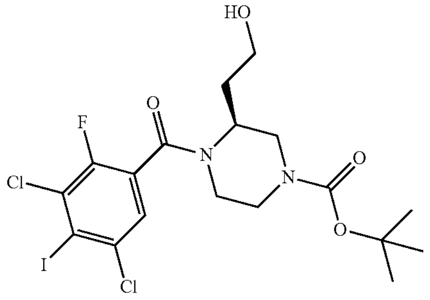 [SMILES: CC(C)(C)OC(=O)N1CCN(C(=O)c2cc(Cl)c(I)c(Cl)c2F)[C@@H](CCO)C1]

3,5-Dichloro-2-fluoro-4-iodo-benzoic acid (0.80 g, 2.4 mmol) is added to DIEA (2 mL, 11.5 mmol) in THF (22 mL) followed by HATU (0.84 g, 2.2 mmol) and stirred for 1 hour. tert-Butyl (3S)-3-(2-hydroxyethyl)piperazine-1-carboxylate (0.50 g, 2.2 mmol) is then added and the reaction mixture is refluxed overnight. After this time, 5N NaOH is added and the reaction is stirred for 1 hour. EtOAc and water are added. The aqueous layer is extracted two times with EtOAc. The combined organic extracts are dried over anhydrous magnesium sulfate, filtered, and concentrated in vacuo. The crude mixture is purified by silica gel flash chromatography eluting with EtOAc:hexane (30:70) to give the title compound (0.858 g, 72%). ES/MS m/z ($^{35}Cl/^{37}Cl$) 491/493 $[M-t-Bu+H]^+$.

TABLE 3

Compounds made in a manner essentially analogous to the method of Preparation 26.

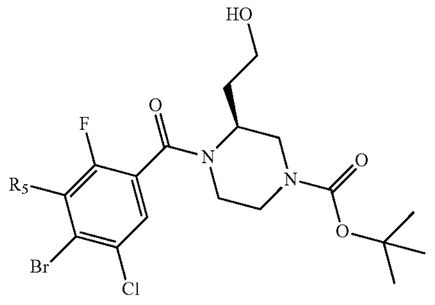

| Preparation | $R_5$ | Compound Name | ES/MS m/z (M + H) |
|---|---|---|---|
| 27 | F | tert-Butyl (3S)-4-(4-bromo-5-chloro-2,3-difluoro-benzoyl)-3-(2-hydroxyethyl) piperazine-1-carboxylate | 427.0/429.0 |
| 28 | H | tert-Butyl (3S)-4-(4-bromo-5-chloro-2-fluoro-benzoyl)-3-(2-hydroxyethyl) piperazine-1-carboxylate | 408.8/410.8 |

Preparation 29 tert-Butyl (13aS)-8,10-dichloro-9-iodo-6-oxo-1,3,4,12,13,13a-hexahydropyrazino[2,1-d][1,5]benzoxazocine-2-carboxylate

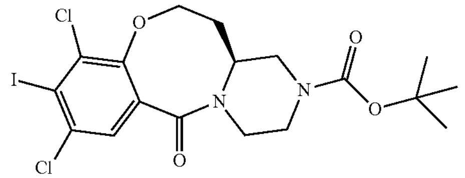 [SMILES: CC(C)(C)OC(=O)N1CCN2C(=O)c3cc(Cl)c(I)c(Cl)c3OCC[C@H]2C1]

tert-Butyl (3S)-4-(3,5-dichloro-2-fluoro-4-iodo-benzoyl)-3-(2-hydroxyethyl)piperazine-1-carboxylate (4.438 g, 8.110 mmol) in DMF (100 mL) is cooled to 0° C. and then to the solution is added NaH (60 mass % in paraffin oil) (0.81 g, 20 mmol). After 1 hour at 0° C., the reaction mixture is quenched with saturated aqueous sodium bicarbonate solution. Water and EtOAc are added. The aqueous layer is extracted twice with EtOAc. The combined organic extracts are washed twice with 0.2 M aqueous lithium chloride, dried over anhydrous magnesium sulfate, filtered, and concentrated in vacuo. The crude mixture is purified via silica gel flash chromatography eluting with 30-50% EtOAc/hexane to give the title compound (3.394 g, 79%). ES/MS m/z ($^{35}Cl/^{37}Cl$) 471/473 $[M-t-Bu+H]^+$.

TABLE 4

Compounds made in a manner essentially analogous to the method of Preparation 29.

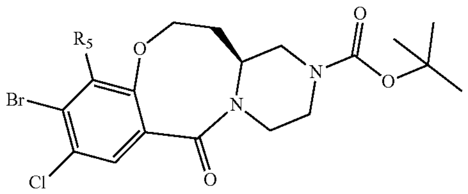

| Preparation | $R_5$ | Compound Name | ES/MS m/z (M + H) |
|---|---|---|---|
| 30 | F | tert-Butyl (13aS)-9-bromo-8-chloro-10-fluoro-6-oxo-1,3,4,12,13,13a-hexahydropyrazino[2,1-d][1,5]benzoxazocine-2-carboxylate | 406.9/409.0 |
| 31 | H | tert-Butyl (13aS)-9-bromo-8-chloro-6-oxo-1,3,4,12,13,13a-hexahydropyrazino[2,1-d][1,5]benzoxazocine-2-carboxylate | 388.8/390.8 |

Preparation 32 tert-Butyl (13aS)-8-chloro-6-oxo-9-(4,4,5,5-tetramethyl-1,3,2-dioxaborolan-2-yl)-1,3,4,12,13,13a-hexahydropyrazino[2,1-d][1,5]benzoxazocine-2-carboxylate

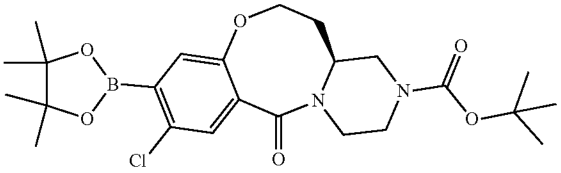 [SMILES: CC(C)(C)OC(=O)N1CCN2C(=O)c3cc(Cl)c(B4OC(C)(C)C(C)(C)O4)cc3OCC[C@H]2C1]

The title compound is prepared from tert-butyl (13aS)-9-bromo-8-chloro-6-oxo-1,3,4,12,13,13a-hexahydropyrazino [2,1-d][1,5]benzoxazocine-2-carboxylate in a manner essentially analogous to the method of preparation 13. ES/MS m/z ($^{35}Cl/^{37}Cl$) 391/393 $[M-Boc+H]^+$.

Preparation 33 tert-Butyl (13aS)-9-(1,3-benzothiazol-4-yl)-8,10-dichloro-6-oxo-1,3,4,12,13,13a-hexahydropyrazino [2,1-d][1,5]benzoxazocine-2-carboxylate

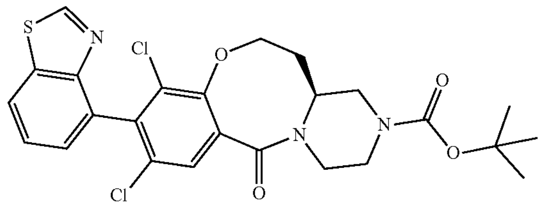 [SMILES: CC(C)(C)OC(=O)N1CCN2C(=O)c3cc(Cl)c(-c4cccc5scnc45)c(Cl)c3OCC[C@H]2C1]

To a vial are added sequentially tert-butyl (13aS)-8,10-dichloro-9-iodo-6-oxo-1,3,4,12,13,13a-hexahydropyrazino [2,1-d][1,5]benzoxazocine-2-carboxylate (110 mg, 0.21 mmol), 4-(4,4,5,5-tetramethyl-1,3,2-dioxaborolan-2-yl)-1,3-benzothiazole (124 mg, 0.31 mmol), [1,1'-bis(diphenylphosphino)ferrocene]dichloropalladium(II) (14 mg, 0.02 mmol) and potassium phosphate tribasic (69 mg, 0.31 mmol). 1,4-Dioxane (2 mL) and water (0.7 mL) are added under nitrogen and the mixture is sparged with nitrogen for 10 minutes. The vial is placed in a heating block preheated to 80° C. and the mixture is stirred for 40 minutes. The mixture is combined with that from an identical reaction conducted on a 15 mg (0.03 mmol) scale and the combined crude mixtures are diluted with DCM and transferred to a separatory funnel. The organic layer is washed with water and the aqueous layer is extracted again with DCM. The combined organics are dried over sodium sulfate, filtered, and concentrated in vacuo. The resulting residue is purified via silica gel flash chromatography eluting with 0-100% EtOAc/hexanes to give the title compound (157 mg, 65% purity, 91%). ES/MS m/z ($^{35}Cl/^{37}Cl$) 534.2/536.2 $[M+H]^+$.

TABLE 5

Compounds made in a manner essentially analogous to the method of Preparation 33.

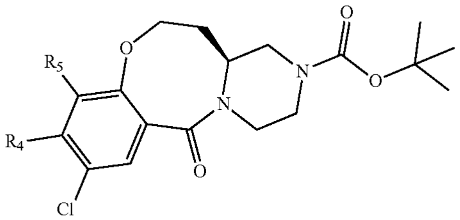

| Preparation | $R_4$ | $R_5$ | Compound Name | ES/MS m/z (M + H) |
|---|---|---|---|---|
| 34 | 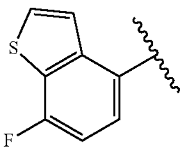 [SMILES: *c1ccc(F)c2sccc12] | Cl | tert-Butyl (13aS)-8,10-dichloro-9-(7-fluorobenzothiophen-4-yl)-6-oxo-1,3,4,12,13,13a-hexahydropyrazino[2,1-d][1,5]benzoxazocine-2-carboxylate | 495.2/497.0 |

TABLE 5-continued

Compounds made in a manner essentially analogous to the method of Preparation 33.

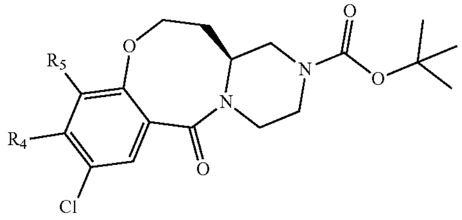

| Preparation | $R_4$ | $R_5$ | Compound Name | ES/MS m/z (M + H) |
|---|---|---|---|---|
| 35 | 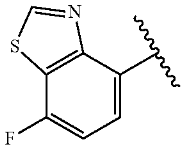 [SMILES: *c1ccc(F)c2scnc12] | Cl | tert-Butyl (13aS)-8,10-dichloro-9-(7-fluoro-1,3-benzothiazol-4-yl)-6-oxo-1,3,4,12,13,13a-hexahydropyrazino[2,1-d][1,5]benzoxazocine-2-carboxylate | 496.0/498.0 |
| 36 | 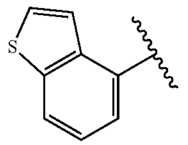 [SMILES: *c1cccc2sccc12] | Cl | tert-butyl (13aS)-9-(benzothiophen-4-yl)-8,10-dichloro-6-oxo-1,3,4,12,13,13a-hexahydropyrazino[2,1-d][1,5]benzoxazocine-2-carboxylate | 477.2/479.2 |
| 37 | 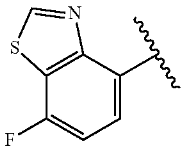 [SMILES: *c1ccc(F)c2scnc12] | F | tert-butyl (13aS)-8-chloro-10-fluoro-9-(7-fluoro-1,3-benzothiazol-4-yl)-6-oxo-1,3,4,12,13,13a-hexahydropyrazino[2,1-d][1,5]benzoxazocine-2-carboxylate | 480.2/482.2 |

Preparation 38 tert-Butyl (13aS)-9-(benzothiophen-4-yl)-8-chloro-6-oxo-1,3,4,12,13,13a-hexahydropyrazino[2,1-d][1,5]benzoxazocine-2-carboxylate

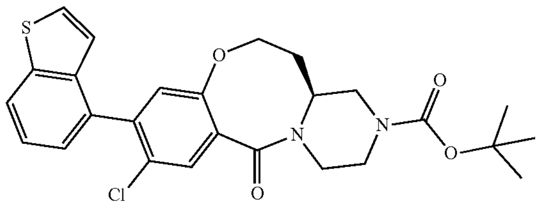 [SMILES: CC(C)(C)OC(=O)N1CCN2C(=O)c3cc(Cl)c(-c4cccc5sccc45)cc3OCC[C@H]2C1]

tert-Butyl (13aS)-8-chloro-6-oxo-9-(4,4,5,5-tetramethyl-1,3,2-dioxaborolan-2-yl)-1,3,4,12,13,13a-hexahydropyrazino[2,1-d][1,5]benzoxazocine-2-carboxylate (200 mg, 0.340 mmol), 4-bromobenzothiophene (80 mg, 0.375 mmol), 1,1'-bis(di-tert-butylphosphino)ferrocene palladium dichloride (23 mg, 0.035 mmol) and potassium carbonate (141 mg, 1.020 mmol) are suspended in 1,4-dioxane (3.4 mL) and water (1.13 mL). The mixture is sparged with nitrogen for 10 minutes and then stirred at 50° C. for 1 hour. After this time, the mixture is cooled to ambient temperature and diluted with EtOAc (100 mL). The solution is washed with saturated aqueous sodium chloride solution (100 mL), dried over sodium sulfate, filtered, and concentrated in vacuo. The resulting residue is purified via silica gel flash chromatography eluting with hexanes followed by 10-50% EtOAc/hexanes to give the title compound as a white solid (137 mg, 80.5%). ES/MS m/z ($^{35}Cl/^{37}Cl$) 499/501 $[M+H]^+$.

TABLE 6

Compounds made in a manner essentially analogous to the method of Preparation 38.

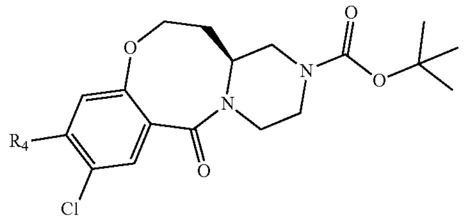

| Prep | $R_4$ | Compound Name | ES/MS m/z (M + H) |
|---|---|---|---|
| 39 | 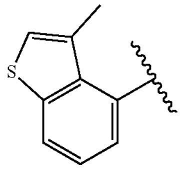 [SMILES: *c1cccc2scc(C)c12] | tert-Butyl (13aS)-8-chloro-9-(3-methylbenzothiophen-4-yl)-6-oxo-1,3,4,12,13,13a-hexahydropyrazino[2,1-d][1,5]benzoxazocine-2-carboxylate | 513.2/515.2 |
| 40 | 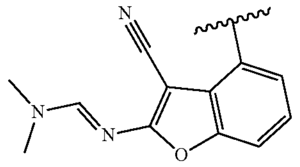 [SMILES: *c1cccc2oc(/N=C/N(C)C)c(C#N)c12] | tert-Butyl (13aS)-8-chloro-9-[3-cyano-2-[(E)-dimethylaminomethyleneamino]benzofuran-4-yl]-6-oxo-1,3,4,12,13,13a-hexahydropyrazino[2,1-d][1,5]benzoxazocine-2-carboxylate | 522.6/524.6 |
| 41 | 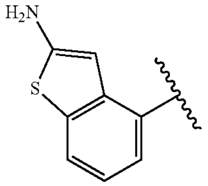 [SMILES: *c1cccc2sc(N)cc12] | tert-Butyl (13aS)-9-(2-aminobenzothiophen-4-yl)-8-chloro-6-oxo-1,3,4,12,13,13a-hexahydropyrazino[2,1-d][1,5]benzoxazocine-2-carboxylate | 513.5/515.5 |
| 42 | 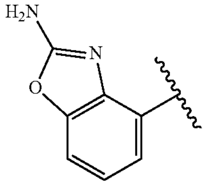 [SMILES: *c1cccc2oc(N)nc12] | tert-Butyl (13aS)-9-(2-amino-1,3-benzoxazol-4-yl)-8-chloro-6-oxo-1,3,4,12,13,13a-hexahydropyrazino[2,1-d][1,5]benzoxazocine-2-carboxylate | 499/501 |
| 43 | 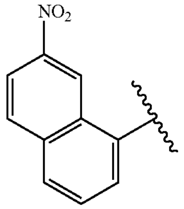 [SMILES: *c1cccc2ccc([N+](=O)[O-])cc12] | tert-Butyl (13aS)-8-chloro-9-(7-nitro-1-naphthyl)-6-oxo-1,3,4,12,13,13a-hexahydropyrazino[2,1-d][1,5]benzoxazocine-2-carboxylate | 482.2/484.2 |
| 44 | 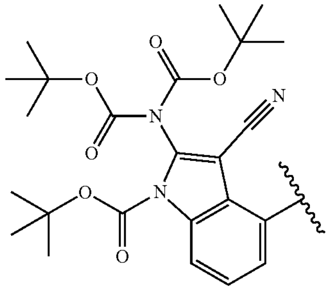 [SMILES: *c1cccc2c1c(C#N)c(N(C(=O)OC(C)(C)C)C(=O)OC(C)(C)C)n2C(=O)OC(C)(C)C] | tert-Butyl (13aS)-9-[2-[bis(tert-butoxycarbonyl)amino]-1-tert-butoxycarbonyl-3-cyano-indol-4-yl]-8-chloro-6-oxo-1,3,4,12,13,13a-hexahydropyrazino[2,1-d][1,5]benzoxazocine-2-carboxylate | 822.2/824.2 |

Preparation 45 tert-Butyl (13aS)-9-(2-amino-3-cyano-benzofuran-4-yl)-8-chloro-6-oxo-1,3,4,12,13,13a-hexahydropyrazino[2,1-d][1,5]benzoxazocine-2-carboxylate

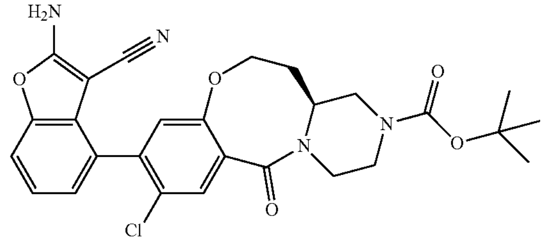 [SMILES: CC(C)(C)OC(=O)N1CCN2C(=O)c3cc(Cl)c(-c4cccc5oc(N)c(C#N)c45)cc3OCC[C@H]2C1]

1N NaOH (0.5 mL, 0.5 mmol) is added to a mixture of tert-butyl (13aS)-8-chloro-9-[3-cyano-2-[(E)-dimethylaminomethyleneamino]benzofuran-4-yl]-6-oxo-1,3,4,12,13,13a-hexahydropyrazino[2,1-d][1,5]benzoxazocine-2-carboxylate (65 mg, 0.112 mmol) in MeOH (5 mL) and heated to 60° C. for three hours. After this time, the reaction mixture is quenched with 5N HCl (0.1 mL) then concentrated in vacuo. The resulting residue is purified via silica gel flash chromatography eluting with 0-100% EtOAc/hexane to give the title compound as a white solid (59 mg, 77%). ES/MS m/z ($^{35}Cl/^{37}Cl$) 522.6/524.6 $[M+H]^+$.

Preparation 46 tert-Butyl (13aS)-9-(7-amino-1-naphthyl)-8-chloro-6-oxo-1,3,4,12,13,13a-hexahydropyrazino[2,1-d][1,5]benzoxazocine-2-carboxylate

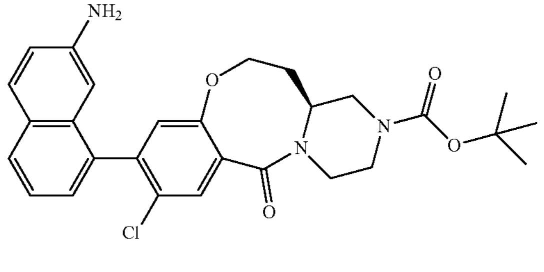 [SMILES: CC(C)(C)OC(=O)N1CCN2C(=O)c3cc(Cl)c(-c4cccc5ccc(N)cc45)cc3OCC[C@H]2C1]

5% Pt/C (S) (0.013 g, 0.066 mmol) is added to a vessel which is purged with nitrogen. EtOAc (5 mL) is added to the vessel followed by tert-butyl (13aS)-8-chloro-9-(7-nitro-1-naphthyl)-6-oxo-1,3,4,12,13,13a-hexahydropyrazino[2,1-d][1,5]benzoxazocine-2-carboxylate (0.050 g, 0.093 mmol). The vessel is sealed, purged with nitrogen, purged with hydrogen, and pressurized under hydrogen (60 psi). The vessel is placed on a Parr shaker for 1 hour at ambient temperature. After this time, the reaction mixture is filtered, and concentrated in vacuo. Another batch of 100 mg of the nitro compound was reduced in a similar manner as described and the two batches were combined and concentrated in vacuo to give the title compound which is used as is in the next step (0.155 g, 99+%). ES/MS m/z 508.2/510.2 $[M+H]^+$.

Preparation 47

(13aS)-9-(1,3-Benzothiazol-4-yl)-8,10-dichloro-2,3,4,12,13,13a-hexahydro-1H-pyrazino[2,1-d][1,5]benzoxazocin-6-one

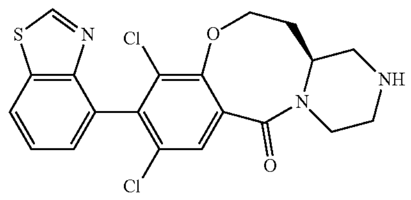 [SMILES: O=C1c2cc(Cl)c(-c3cccc4scnc34)c(Cl)c2OCC[C@H]2CNCCN12]

A flask is charged with tert-butyl (13aS)-9-(1,3-benzothiazol-4-yl)-8,10-dichloro-6-oxo-1,3,4,12,13,13a-hexahydropyrazino[2,1-d][1,5]benzoxazocine-2-carboxylate (157 mg, 65% purity, 0.19 mmol) and DCM (2.5 mL) is added followed by TFA (3 mL). The mixture is stirred at ambient temperature for 30 minutes, after which the solvent is removed in vacuo. The mixture is co-evaporated with DCM three times to remove excess TFA. The resulting residue is loaded onto an ion exchange cartridge and flushed with MeOH, 2N $NH_3$ in MeOH, and again with MeOH. The basic fraction is concentrated in vacuo to give the title compound (86 mg, 99+%). ES/MS m/z ($^{35}Cl/^{37}Cl$) 434.2/436.2 $[M+H]^+$.

TABLE 7

Compounds made in a manner essentially analogous to the method of Preparation 47.

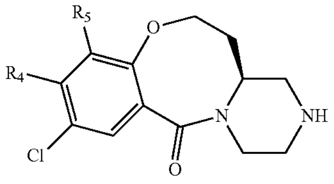

| Preparation | $R_4$ | $R_5$ | Compound Name | ES/MS m/z (M + H) |
|---|---|---|---|---|
| 48 | 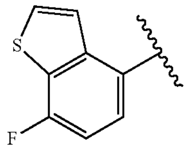 [SMILES: *c1ccc(F)c2sccc12] | Cl | (13aS)-8,10-Dichloro-9-(7-fluorobenzothiophen-4-yl)-2,3,4,12,13,13a-hexahydro-1H-pyrazino[2,1-d][1,5]benzoxazocin-6-one | 451.2/453.2 |
| 49 | 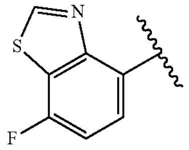 [SMILES: *c1ccc(F)c2scnc12] | Cl | (13aS)-8,10-Dichloro-9-(7-fluoro-1,3-benzothiazol-4-yl)-2,3,4,12,13,13a-hexahydro-1H-pyrazino[2,1-d][1,5]benzoxazocin-6-one | 452.0/454.0 |
| 50 | 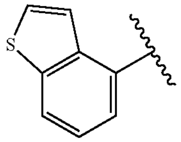 | H | (13aS)-9-(Benzothiophen-4-yl)-8-chloro-2,3,4,12,13,13a-hexahydro-1H-pyrazino[2,1-d][1,5]benzoxazocin-6-one | 399.2/401.2 |
| 51 | 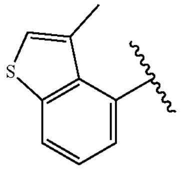 [SMILES: *c1cccc2scc(C)c12] | H | (13aS)-8-Chloro-9-(3-methylbenzothiophen-4-yl)-2,3,4,12,13,13a-hexahydro-1H-pyrazino[2,1-d][1,5]benzoxazocin-6-one | 413.2/415.2 |
| 52 | 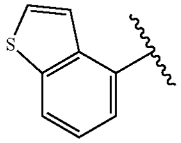 [SMILES: *c1cccc2sccc12] | Cl | (13aS)-9-(Benzothiophen-4-yl)-8,10-dichloro-2,3,4,12,13,13a-hexahydro-1H-pyrazino[2,1-d][1,5]benzoxazocin-6-one | 433.2/435.2 |
| 53 | 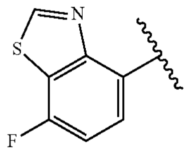 [SMILES: *c1ccc(F)c2scnc12] | F | (13aS)-8-Chloro-10-fluoro-9-(7-fluoro-1,3-benzothiazol-4-yl)-2,3,4,12,13,13a-hexahydro-1H-pyrazino[2,1-d][1,5]benzoxazocin-6-one | 436.2 |
| 54 | 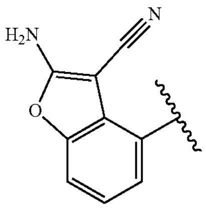 [SMILES: *c1cccc2oc(N)c(C#N)c12] | H | 4-[(13aS)-8-Chloro-6-oxo-2,3,4,12,13,13a-hexahydro-1H-pyrazino[2,1-d][1,5]benzoxazocin-9-yl]-2-amino-benzofuran-3-carbonitrile | 422.6/424.6 |

TABLE 7-continued

Compounds made in a manner essentially analogous to the method of Preparation 47.

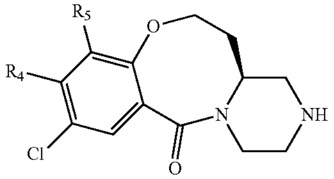

| Preparation | $R_4$ | $R_5$ | Compound Name | ES/MS m/z (M + H) |
|---|---|---|---|---|
| 55 | 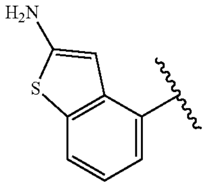 [SMILES: *c1cccc2sc(N)cc12] | H | (13aS)-9-(2-Aminobenzothiophen-4-yl)-8-chloro-2,3,4,12,13,13a-hexahydro-1H-pyrazino[2,1-d][1,5]benzoxazocin-6-one | 413.6/415.6 |
| 56 | 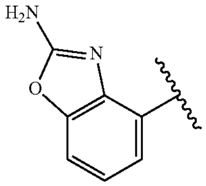 [SMILES: *c1cccc2oc(N)nc12] | H | (13aS)-9-(2-Amino-1,3-benzoxazol-4-yl)-8-chloro-2,3,4,12,13,13a-hexahydro-1H-pyrazino[2,1-d][1,5]benzoxazocin-6-one | 399/401 |
| 57 | 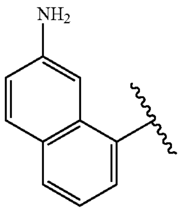 [SMILES: *c1cccc2ccc(N)cc12] | H | (13aS)-9-(7-Amino-1-naphthyl)-8-chloro-2,3,4,12,13,13a-hexahydro-1H-pyrazino[2,1-d][1,5]benzoxazocin-6-one | 408/410 |
| 58 | 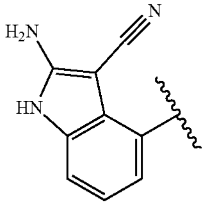 [SMILES: *c1cccc2[nH]c(N)c(C#N)c12] | H | 4-[(13aS)-8-Chloro-6-oxo-2,3,4,12,13,13a-hexahydro-1H-pyrazino[2,1-d][1,5]benzoxazocin-9-yl]-2-amino-1H-indole-3-carbonitrile | 422.4/424.4 |

Preparation 59

Kras Probe

N-(2-{2-[2-({6-Chloro-8-fluoro-7-(3-hydroxynaphthalen-1-yl)-4-[4-(prop-2-enoyl)piperazin-1-yl]quinazolin-2-yl}amino)ethoxy]ethoxy}ethyl)-5-[(3aS, 4S,6aR)-2-oxohexahydro-1H-thieno[3,4-d] 50enzoxaze-4-yl]pentanamide

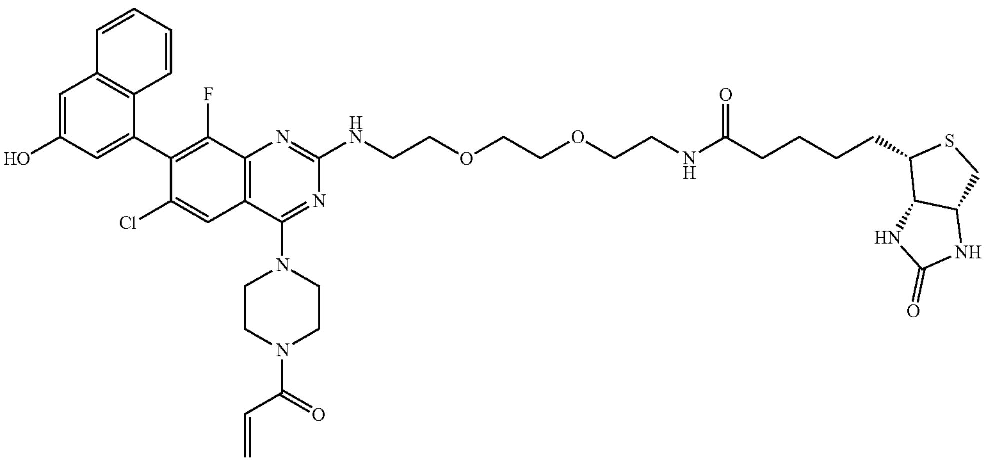 [SMILES: C=CC(=O)N1CCN(c2nc(NCCOCCOCCNC(=O)CCCC[C@@H]3SC[C@@H]4NC(=O)N[C@@H]43)nc3c(F)c(-c4cc(O)cc5ccccc45)c(Cl)cc23)CC1]

Step A: tert-Butyl 4-(7-bromo-2,6-dichloro-8-fluoroquinazolin-4-yl)piperazine-1-carboxylate (0.51 g, 1.1 mmol) and IPA (5 mL) are combined in a microwave vessel. DIPEA (0.55 mL, 3.3 mmol) and 5-[(3aS,4S,6aR)-2-oxohexahydro-1H-thieno[3,4-d]50enzoxaze-4-yl]-N-[2-[2-(2-aminoethoxy)ethoxy]ethyl]pentanamide (0.48 g, 1.32 mmol) are added and the mixture is heated to 120° C. in a microwave reactor for six hours. After this time the mixture is diluted with saturated aqueous ammonium chloride solution and 25% IPA in $CHCl_3$ and the layers are separated. The organic layer is washed with saturated aqueous sodium chloride solution, dried over anhydrous sodium sulfate, filtered, and concentrated in vacuo. The resulting residue is purified by normal phase chromatography, eluting with a 50-100% B in A gradient (A: hexanes, B: 10% MeOH in DCM), to give the tert-butyl 4-{7-bromo-6-chloro-8-fluoro-2-[(2-{2-[2-({5-[(3aS,4S,6aR)-2-oxohexahydro-1H-thieno[3,4-d]51enzoxaze-4-yl]pentanoyl}amino) ethoxy]ethoxy}ethyl)amino] quinazolin-4-yl}piperazine-1-carboxylate as a yellow solid (0.68 g, 78%). ES/MS m/z: 819 (M+H).

Step B: tert-Butyl 4-{7-bromo-6-chloro-8-fluoro-2-[(2-{2-[2-({5-[(3aS,4S,6aR)-2-oxohexahydro-1H-thieno[3,4-d] 51enzoxaze-4-yl]pentanoyl}amino)ethoxy]ethoxy}ethyl) amino]quinazolin-4-yl}piperazine-1-carboxylate (0.30 g, 0.37 mmol), 1,4-dioxane (4 mL) and water (0.75 mL) are combined. Potassium carbonate (0.24 g, 1.11 mmol), 4-(4, 4,5,5-tetramethyl-1,3,2-dioxaborolan-2-yl)naphthalen-2-ol (0.20 g, 0.74 mmol), and tetrakis(triphenylphosphine) palladium(0) (0.085 g, 0.074 mmol) are added and the mixture is stirred at 85° C. under nitrogen for 12 hours. After this time, the mixture is cooled to ambient temperature and filtered to remove solids. The filtrate is diluted with saturated aqueous ammonium chloride solution and EtOAc and the layers are separated. The organic layer is washed with saturated aqueous sodium chloride solution, dried over anhydrous sodium sulfate, filtered, and concentrated in vacuo. The resulting residue is purified by normal phase chromatography, eluting with a 90-100% B in A gradient (A: hexanes, B: 10% MeOH in DCM), to give tert-butyl 4-{6-chloro-8-fluoro-7-(3-hydroxynaphthalen-1-yl)-2-[(2-{2-[2-({5-[(3aS,4S,6aR)-2-oxohexahydro-1H-thieno[3,4-d]51enzoxaze-4-yl]pentanoyl}amino) ethoxy]ethoxy}ethyl)amino] quinazolin-4-yl}piperazine-1-carboxylate as a yellow solid (0.31 g, 96%). ES/MS m/z: 881 (M+H).

Step C: A solution of tert-butyl 4-{6-chloro-8-fluoro-7-(3-hydroxynaphthalen-1-yl)-2-[(2-{2-[2-({5-[(3aS,4S,6aR)-2-oxohexahydro-1H-thieno[3,4-d]51enzoxaze-4-yl] pentanoyl}amino)ethoxy]ethoxy}ethyl)amino]quinazolin-4-yl}piperazine-1-carboxylate (0.31 g, 0.35 mmol) in MeOH (4 mL) is cooled to 0° C. HCl (3 M in MeOH, 6 mL, 17.5 mmol) is added and the mixture is stirred at 0° C. for 30 minutes before allowing to warm to ambient temperature. After ~18 hours, the reaction mixture is concentrated in vacuo. The residue is diluted with DCM and concentrated in vacuo again. The resulting residue is diluted with hexanes and stirred at ambient temperature for two hours. The resulting solid is filtered and dried under vacuum to give N-{2-[2-(2-{[6-chloro-8-fluoro-7-(3-hydroxynaphthalen-1-yl)-4-(piperazin-1-yl)quinazolin-2-yl]amino}ethoxy) ethoxy]ethyl}-5-[(3aS,4S,6aR)-2-oxohexahydro-1H-thieno [3,4-d]52enzoxaze-4-yl]pentanamide hydrogen chloride. This hydrochloride salt (0.19 g, 0.23 mmol) is neutralized by combining with DIEA (0.16 mL, 0.92 mmol) in DCM (2.5 mL). The mixture is cooled to −78° C. and acryloyl chloride (0.5 M in DCM, 0.4 mL, 0.21 mmol) is added. After 30 minutes, the mixture is warmed to ambient temperature. After one hour, the mixture is diluted with MeOH (1 mL) and concentrated in vacuo. The resulting residue is purified by reverse phase chromatography, eluting with a 35-60% B in A gradient (A: 10 mM aqueous $NH_4HCO_3$ with 5% MeOH; B: ACN), to give the title compound as a white solid (0.027 g, 14%). ES/MS m/z: 835 (M+H).

Example 1

(13aS)-9-(1,3-Benzothiazol-4-yl)-8,10-dichloro-2-prop-2-enoyl-1,3,4,12,13,13a-hexahydropyrazino[2,1-d][1,5]benzoxazocin-6-one

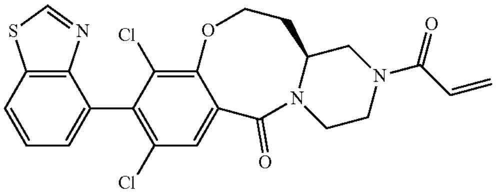 [SMILES: C=CC(=O)N1CCN2C(=O)c3cc(Cl)c(-c4cccc5scnc45)c(Cl)c3OCC[C@H]2C1]

A vial is charged with (13aS)-9-(1,3-benzothiazol-4-yl)-8,10-dichloro-2,3,4,12,13,13a-hexahydro-1H-pyrazino[2,1-d][1,5]benzoxazocin-6-one (86 mg, 0.20 mmol), DCM (3.6 mL) and DIEA (0.07, 0.40 mmol). The mixture is cooled to −78° C. and a solution of acryloyl chloride (0.1 mL, 0.1 mmol, 1M in DCM) is added slowly. After stirring for 10 minutes, MeOH (1.8 mL) is added and the mixture is warmed to ambient temperature. The mixture is diluted with DCM and washed with saturated aqueous sodium chloride solution. The aqueous layer is extracted with EtOAc and the organic layers are combined, dried over sodium sulfate, filtered, and concentrated in vacuo. The resulting residue is purified via silica gel flash chromatography eluting with 50-100% EtOAc/hexanes to give the title compound (62 mg, 64%) as a mixture of two rotamers. ES/MS m/z ($^{35}$Cl/$^{37}$Cl) 488.2/490.2 [M+H]$^+$. The two atropisomers are separated using chiral HPLC (Chiralpak AD-H 30×250 mm column, 30 mL/min flow rate, 100% MeOH). The desired atropisomer is eluted at 5.6 min.

TABLE 8

Compounds made in a manner essentially analogous to the method of Example 1.

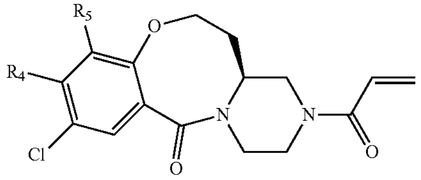

| Example | $R_4$ | $R_5$ | Compound Name | ES/MS m/z (M + H) |
|---|---|---|---|---|
| 2 | 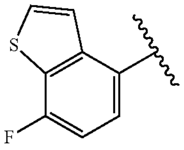 | Cl | (13aS)-8,10-Dichloro-9-(7-fluorobenzothiophen-4-yl)-2-prop-2-enoyl-1,3,4,12,13,13a-hexahydropyrazino[2,1-d][1,5]benzoxazocin-6-one | 505/507 |
| 3 | 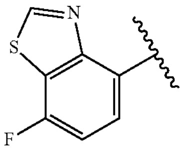 | Cl | (13aS)-8,10-Dichloro-9-(7-fluoro-1,3-benzothiazol-4-yl)-2-prop-2-enoyl-1,3,4,12,13,13a-hexahydropyrazino[2,1-d][1,5]benzoxazocin-6-one | 506.2/508.2 |
| 4 | 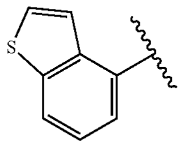 [SMILES: *c1cccc2sccc12] | H | (13aS)-9-(Benzothiophen-4-yl)-8-chloro-2-prop-2-enoyl-1,3,4,12,13,13a-hexahydropyrazino[2,1-d][1,5]benzoxazocin-6-one | 453.2/455.2 |
| 5 | 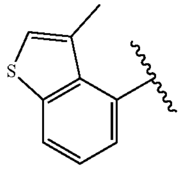 [SMILES: *c1cccc2scc(C)c12] | H | (13aS)-8-Chloro-9-(3-methylbenzothiophen-4-yl)-2-prop-2-enoyl-1,3,4,12,13,13a-hexahydropyrazino[2,1-d][1,5]benzoxazocin-6-one | 467.2/469.2 |
| 6 | 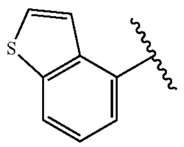 [SMILES: *c1cccc2sccc12] | Cl | (13aS)-9-(Benzothiophen-4-yl)-8,10-dichloro-2-prop-2-enoyl-1,3,4,12,13,13a-hexahydropyrazino[2,1-d][1,5]benzoxazocin-6-one | 487.2/489.2 |

TABLE 8-continued

Compounds made in a manner essentially analogous to the method of Example 1.

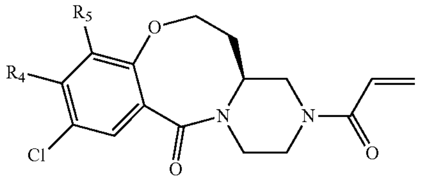

| Example | $R_4$ | $R_5$ | Compound Name | ES/MS m/z (M + H) |
|---|---|---|---|---|
| 7 | 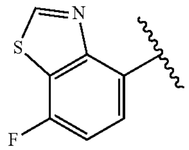 [SMILES: *c1ccc(F)c2scnc12] | F | (13aS)-8-Chloro-10-fluoro-9-(7-fluoro-1,3-benzothiazol-4-yl)-2-prop-2-enoyl-1,3,4,12,13,13a-hexahydropyrazino[2,1-d][1,5]benzoxazocin-6-one | 490.2/492.2 |
| 8 | 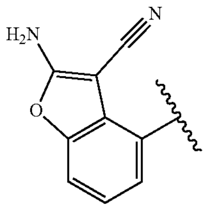 [SMILES: *c1cccc2oc(N)c(C#N)c12] | H | 4-[(13aS)-8-Chloro-6-oxo-2-prop-2-enoyl-1,3,4,12,13,13a-hexahydropyrazino[2,1-d][1,5]benzoxazocin-9-yl]-2-amino-benzofuran-3-carbonitrile | 477/479 |
| 9 | 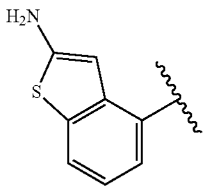 | H | (13aS)-9-(2-Aminobenzothiophen-4-yl)-8-chloro-2-prop-2-enoyl-1,3,4,12,13,13a-hexahydropyrazino[2,1-d][1,5]benzoxazocin-6-one | 468/470 |

Example 10

(13aS)-9-(2-Amino-1,3-benzoxazol-4-yl)-8-chloro-2-prop-2-enoyl-1,3,4,12,13,13a-hexahydropyrazino[2,1-d][1,5]benzoxazocin-6-one

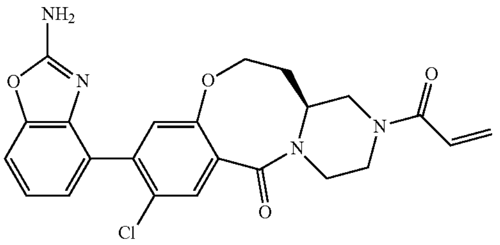 [SMILES: C=CC(=O)N1CCN2C(=O)c3cc(Cl)c(-c4cccc5oc(N)nc45)cc3OCC[C@H]2C1]

Acryloyl chloride (14.7 μl, 0.175 mmol) is added at 0° C. to a vigorously stirring, biphasic mixture of (13as)-9-(2-amino-1,3-benzoxazol-4-yl)-8-chloro-2,3,4,12,13,13a-hexahydro-1h-pyrazino[2,1-d][1,5]benzoxazocin-6-one (70 mg, 0.176 mmol) and potassium carbonate (73 mg, 0.528 mmol) in EtOAc (2 mL) and water (2 mL). The resulting mixture is stirred at 0° C. for 15 minutes. After this time, water and DCM are added and the layers are separated. The aqueous layer is extracted with DCM twice more. The organics are combined, passed through a hydrophobic frit, and concentrated in vacuo. The residue is purified via reverse phase chromatography to give the title compound as a white solid (54 mg, 68%). ES/MS m/z ($^{35}Cl/^{37}Cl$) 453/455 $[M+H]^+$.

TABLE 9

Compounds made in a manner essentially analogous to the method in Example 10.

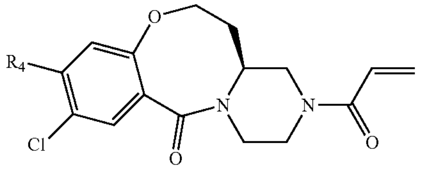

| Example | $R_4$ | Compound Name | ES/MS m/z (M + H) |
|---|---|---|---|
| 11 | 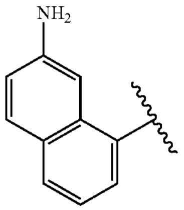 | (13aS)-9-(7-Amino-1-naphthyl)-8-chloro-2-prop-2-enoyl-1,3,4,12,13,13a-hexahydropyrazino[2,1-d][1,5]benzoxazocin-6-one | 462/464 |
| 12 | 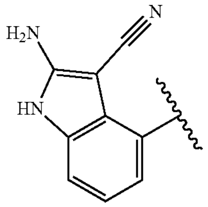 [SMILES: *c1cccc2[nH]c(N)c(C#N)c12] | 4-[(13aS)-8-Chloro-6-oxo-2-prop-2-enoyl-1,3,4,12,13,13a-hexahydropyrazino[2,1-d][1,5]benzoxazocin-9-yl]-2-amino-1H-indole-3-carbonitrile | 476.4 |

BIOLOGICAL ASSAYS

The following assays demonstrate that the exemplified compounds are inhibitors of KRas G12C and inhibit growth of certain tumors in vitro and/or in vivo.

KRas G12C Probe Occupancy TR-FRET Assay

The purpose of this assay is to measure the ability of an inhibitor to compete with a probe for binding to and covalently modifying KRas G12C at codon 12. The signal is generated by the time-resolved transfer of fluorescence between europium on an antibody bound to KRas G12C Europium-labeled Anti-Histidine Tag Antibody LanthaScreen (the Eu Anti-His antibody) and fluorescent Tracer 647 (Alexa Fluor™) bound to KRas G12C through streptavidin and a biotinylated inhibitor (the "KRas Probe", see Preparation 59).

Inhibitors are tested in dose response format from 10 mM stocks in 100% DMSO. The Labycyte Echo® 555 is used to dilute and transfer 100 nL per well containing a 10 point, 2.8-fold serial dilution to an assay plate. Two copies of the assay plate are prepared to measure the potency after 5 and 60 minutes incubation of the inhibitor with KRas G12C. His-tagged KRas G12C (20 nM) is added to the plates in assay buffer (20 mM Tris-HCl, pH 7.5, 0.01% TX-100, and 1 mM DTT). After 5 or 60 minutes incubation, 1 μM KRas Probe is added and allowed to covalently modify free KRas G12C for 1 hour. This is diluted 4-fold in buffer containing Eu Anti-His antibody and Streptavidin-Coated Tracer 647 (both from Life Technologies) to achieve KRas G12C (5 nM), Anti-His Antibody (2 nM), KRas Probe (300 nM), and Streptavidin Coated Tracer 647 (500 nM). After 30 minutes, the fluorescent signal is read on an Envision™ Plate Reader (excitation at 340 nM, tracer emission (em) at 665 nM, and antibody emission at 615 nM). Maximum control wells lack inhibitor and minimum control wells lack both inhibitor and KRas G12C. The signal ratio (em at 665/em at 615) is converted to percent inhibition using the following equation: % Inhibition=100−[(Test Compound Signal−Median Minimum Signal)/(Median Maximum Signal−Median Minimum Signal)×100]. The $IC_{50}$ is determined by fitting the percent inhibition at each inhibitor concentration to the four parameter nonlinear logistic equation using Genedata Screener®: y=(A+((B−A)/(1+((C/x)^D)))) where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds within the scope of Formula I are evaluated in this assay substantially as described above, exhibiting KRas G12C inhibitor activity by competing with a probe for binding to and covalently modifying KRas G12C at codon 12. Exemplified compounds exhibit $IC_{50}$s in a range of 20-425 nM with the compound of Example 2 exhibiting a relative $IC_{50}$ in this assay of 34 nM.

H358 Cellular Phospho-ERK AlphaLISA®

The purpose of this assay is to measure the ability of test compounds to inhibit the phosphorylation of p-ERK1/2, a downstream effector of KRas in human lung cancer cells H358 (ATCC CRL-5807). Briefly, the AlphaLISA® SureFire® Ultra™ p-ERK 1/2 (Thr202/Tyr204) assay is a sandwich immunoassay for quantitative detection of phospho-ERK 1/2 (phosphorylated on Thr202/Tyr204 in ERK1, or Thr185/Tyr187 in ERK2) in cellular lysates using Alpha Technology (Perkin Elmer Cat #ALSU-PERK-A50K).

H358 cells are plated at 40K cells per well in 100 µL media (RPMI 1640, GIBCO Cat #22400-071) containing 10% FBS (GIBCO Cat #: 10082-147) in a 96 well plate (Costar #3596) and are incubated overnight in humid trays at 37° C., 5% $CO_2$. The next morning, 10 µL of serially-diluted (3-fold) test compounds (50 µM top concentration) and 10 µL of controls (Maximum signal wells: 5% DMSO and Minimum signal wells: 2 µM of N-(3-{3-cyclopropyl-5-[(2-fluoro-4-iodophenyl)amino]-6,8-dimethyl-2,4,7-trioxo-3,4,6,7-tetrahydropyrido[4,3-D]pyrimidin-1(2H)-yl}phenyl)acetamide (trametinib, as a positive control) are added to the cell plate and incubated for 2 hours in humid trays at 37° C./5% $CO_2$. Lysis Buffer is prepared at ambient temperature containing a protease and phosphatase inhibitor cocktail. Culture medium is removed by inverting and shaking the cell plate in the sink and then blotting onto a paper towel. Lysis buffer is added to the cell plate (50 µL per well) and the plate is incubated at ambient temperature for 10 minutes on a shaker. For p-ERK detection, acceptor beads are diluted into a suspension mixture with buffer. Using a STARlet liquid handler, 5 µL of acceptor beads and 2 µL of cell lysate are transferred as a single-step in-tip dilution to a 384 well assay plate. The assay plate is sealed with foil and is incubated at ambient temperature for 2 hours. Donor beads are diluted into a suspension mixture with buffer. Using the STARlet, 5 µL of donor beads are added to the assay plate that is then sealed, wrapped with foil. The plate is incubated at ambient temperature for 2 hours in the dark. The assay plate is then read on an EnVision™ Plate Reader (Perkin Elmer) using a luminescence program.

The signal is converted to percent inhibition using the following equation: % Inhibition=100−[(Test Compound Signal−Median Minimum Signal)/(Median Maximum Signal−Median Min Signal)×100]. The Maximum signal is a control well without inhibitor. The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®: y=(A+((B−A)/(1+((C/x)^D)))) where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds within the scope of Formula I are evaluated in this assay substantially as described above, exhibiting an ability to inhibit the phosphorylation of p-ERK1/2. Exemplified compounds exhibit $IC_{50}$s in a range of 89-1430 nM with the compound of Example 2 exhibiting a relative $IC_{50}$ in this assay of 89 nM. This data show that the compounds of the Examples exhibit KRas G12C inhibition activity in this cellular assay.

H358 Cellular Active RAS GTPase ELISA

The purpose of this assay is to measure the ability of test compounds to inhibit constitutive RAS GTPase activity in human lung cancer cells H358 (ATCC CRL-5807). The RAS GTPase ELISA kit (Active Motif Cat #52097) contains a 96-well plate pre-coated with glutathione in order to capture a kit-supplied GST-Raf-RBD protein. Activated RAS (GTP-bound) in cell extracts specifically bind to the Raf-RBD. Bound RAS is detected with a primary antibody that recognizes human KRas. A secondary antibody conjugated with HRP recognizes the primary antibody and a development solution provides a chemiluminescent readout.

H358 cells are plated at 80,000 cells/well in 90 µL serum free media (RPMI 1640, GIBCO) and incubated overnight at 37° C./5% $CO_2$. The next morning, 10 µL of serially-diluted (3-fold) test compounds (500 µM top concentration) and 10 µL of controls (Maximum signal wells: 5% DMSO and Minimum signal wells: 500 µM 1-[4-[6-chloro-8-fluoro-7-(3-hydroxy-1-naphthyl)quinazolin-4-yl]piperazin-1-yl] prop-2-en-1-one, WO2015054572 as an inhibitor) are added to the cell plate and incubated for 2 hours at 37° C./5% $CO_2$. Complete Lysis/Binding Buffer is prepared containing Protease Inhibitor cocktail and GST-Raf-RBD and stored on ice. One hour before cell plate incubation is completed, 50 µL of GST-Raf-RBD is diluted in lysis/binding buffer, and buffer is added to the ELISA assay plate and which is incubated for 1 hour at 4° C. with gently rocking. After 2 hours, the cells are washed with 100 µL ice-cold PBS and lysed with 100 µL lysis/binding buffer. The cell plate is shaken for 10 minutes at ambient temperature. The cell plate is then centrifuged at 1500 rpm for 10 minutes at ambient temperature. During this time, 1× Wash Buffer is prepared at ambient temperature and then is used to wash (3×100 µL) the GST-Raf-RBD coated assay plate. After washing, 50 µL of cell lysate is added to the GST-Raf-RBD coated assay plate and incubated for 1 hour at ambient temperature with gentle shaking. During this incubation period, 1× Antibody Binding Buffer is prepared and brought to ambient temperature. The assay plate is washed 3×100 µL with 1× Wash Buffer and then 50 µL of Primary Antibody (diluted 1:500 in 1× Antibody Binding buffer) is added. The plate is incubated for 1 hour at ambient temperature. The assay plate is washed 3×100 µL with 1× Wash Buffer and then 50 µL of Secondary Antibody (diluted 1:5000 in 1× Antibody Binding buffer) is added and incubated for 1 hour at ambient temperature. The assay plate is washed 4×100 µL with 1× Wash buffer and then 50 µL of chemiluminescent working solution is added at ambient temperature. The assay plate is then read on an EnVision™ Plate Reader (Perkin Elmer) using a luminescence program.

The signal is converted to percent inhibition using the following equation: % Inhibition=100−[(Test Compound Signal−Median Minimum Signal)/(Median Maximum Signal−Median Minimum Signal)×100]. The Maximum signal is a control well without inhibitor. The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®: y=(A+((B−A)/(1+((C/x)^D)))) where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds within the scope of Formula I are evaluated in this assay substantially as described above, exhibiting an ability to inhibit constitutive RAS GTPase activity. Exemplified compounds exhibit $IC_{50}$s in a range of 326-4570 nM with the compound of Example 2 exhibiting a relative $IC_{50}$ in this assay of 326 nM. This data show that the compounds of the Examples exhibit KRas-GTP inhibition activity in this human lung cancer cell culture.

What is claimed is:

1. A compound of the formula:

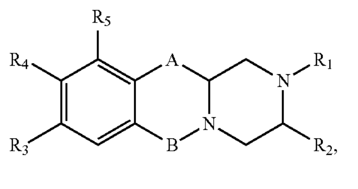

wherein:

A is —$OCH_2$—, —$N(R_6)CH_2$—, —$OCH_2CH_2$—, —$N(R_6)CH_2CH_2$—, —$CH_2OCH_2$—, or —$CH_2N(R_6)CH_2$—;

B is —$CH_2$— or —C(O)—;

R is —CN, —C(O) C≡$CR_8$, or a group of the formula

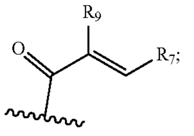

$R_2$ is H, methyl, or —$CH_2CN$;

$R_3$ and $R_5$ are each independently H, halogen, cyclopropyl, —$C_{1-3}$ alkyl-cyclopropyl, —$C_{1-6}$ alkyl optionally substituted 1-3 times with $R^{10}$, or —O—$C_{1-6}$ alkyl optionally substituted 1-3 times with $R^{10}$;

$R_4$ is a group of the formula

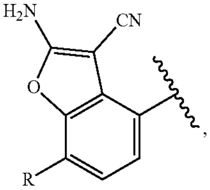
,
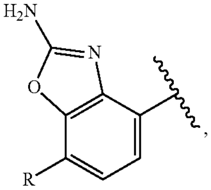
,
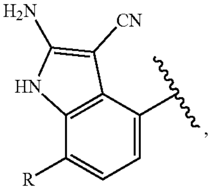
,
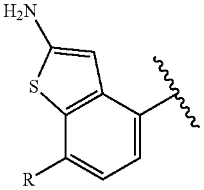
,
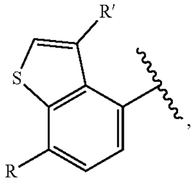
,
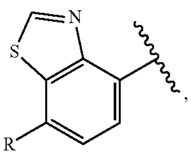
, or
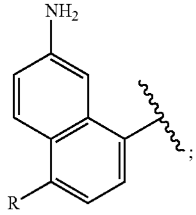
;

R is H, halogen, or —$C_{1-6}$ alkyl optionally substituted 1-3 times with $R_{10}$;

R' is H, or —$C_{1-6}$ alkyl;

$R_6$ is H or —$C_{1-6}$ alkyl optionally substituted 1-3 times with $R_{10}$;

$R_7$ is H, halogen, —$NR_{11}R_{12}$, —$CH_2NR_{11}R_{12}$, —$C_{2-6}$ alkyl optionally substituted 1-3 times with $R_{10}$ or —$NR_{13}R_{14}$, cyclopropyl, —$C_{1-3}$ alkyl cyclopropyl, or —O—$C_{1-6}$ alkyl optionally substituted 1-3 times with $R_{10}$ or —$NR_{13}R_{14}$;

$R_8$ is H, —$C_{1-4}$ alkyl optionally substituted 1-3 times with $R_{10}$, or —$C_{3-6}$ cycloalkyl optionally substituted 1-3 times with $R_{10}$;

$R_9$ is H, halogen, —CN, $C_{3-6}$ cycloalkyl, —$C_{1-3}$ alkyl-$C_{3-6}$ cycloalkyl, or —$C_{1-6}$ alkyl optionally substituted 1-3 times with $R_{10}$;

$R_{10}$ is independently at each occurrence halogen, oxygen, hydroxy, —$C_{1-4}$ alkyl, or —O—$C_{1-4}$ alkyl;

$R_{11}$ and $R_{12}$ are each independently H, —$C_{1-4}$ alkyl, or —$C_{1-4}$ heteroalkyl, wherein $R_{11}$ and $R_{12}$ may combine to form a $C_{5-6}$ heterocycloalkyl; and $R_{13}$ and $R_{14}$ are each independently H or —$C_{1-4}$ alkyl, or a pharmaceutically acceptable salt thereof.

2. The compound according to claim 1, wherein A is —$OCH_2CH_2$—, or a pharmaceutically acceptable salt thereof.

3. The compound according to claim 1, wherein B is —C(O)—, or a pharmaceutically acceptable salt thereof.

4. The compound according to claim 1, wherein $R_1$ is a group of the formula

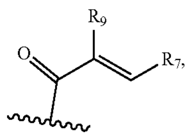

and wherein $R_7$ is H, $—CHF_2$, $—CH_2F$, $—CH_2OH$, $—CH_2OCH_3$, $—CH_2N(CH_3)_2$, or $—CH_2$-morpholine, or a pharmaceutically acceptable salt thereof.

5. The compound according to claim 1, wherein $R_1$ is a group of the formula

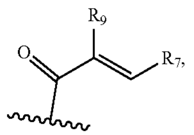

and wherein $R_9$ is H, F, Cl, $—CHF_2$, $—CF_3$, or $—CH_2OH$, or a pharmaceutically acceptable salt thereof.

6. The compound according to claim 1, wherein $R_2$ is H or methyl, or a pharmaceutically acceptable salt thereof.

7. The compound according to claim 1, wherein $R_3$ is H, F, Cl, methyl, methoxy, ethyl, isopropyl, or cyclopropyl or a pharmaceutically acceptable salt thereof.

8. The compound according to claim 1, wherein R is H or F.

9. The compound according to claim 1, wherein $R_4$ is selected from the group consisting of

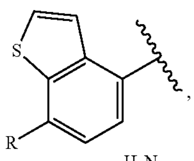

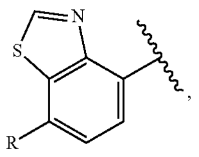

and

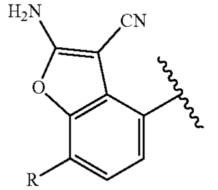

or a pharmaceutically acceptable salt thereof.

10. The compound according to claim 1, wherein $R_5$ is H or Cl, or a pharmaceutically acceptable salt thereof.

11. The compound according to claim 1 is selected from the group consisting of:

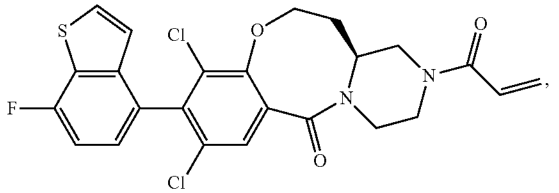

-continued

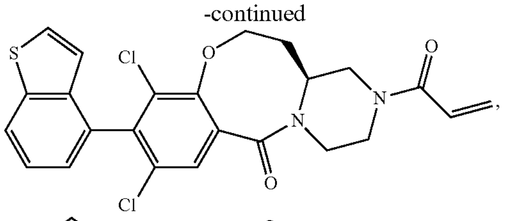

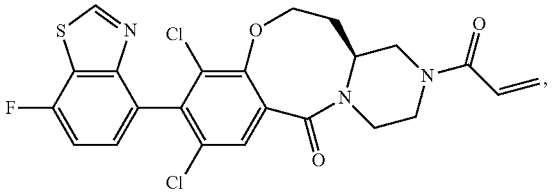

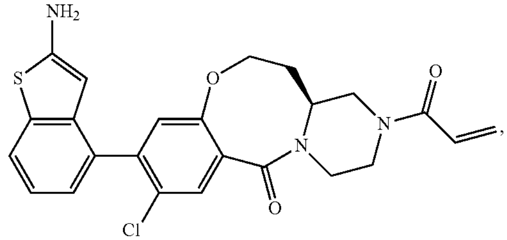

and

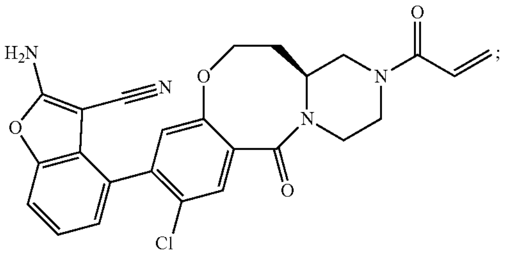

or a pharmaceutically acceptable salt thereof.

12. A pharmaceutical composition comprising a compound according to claim 1, or a pharmaceutically acceptable salt thereof, and a pharmaceutically acceptable carrier, diluent or excipient.

13. A method of treating a patient for cancer, comprising administering to a patient in need thereof, an effective amount of a pharmaceutical composition according to claim 12, wherein the cancer is selected from the group consisting of lung cancer, pancreatic cancer, cervical cancer, esophageal cancer, endometrial cancer, ovarian cancer, cholangiocarcinoma, and colorectal cancer.

14. A method of treating a patient for cancer, comprising administering to a patient in need thereof, an effective amount of a compound according to claim 1, or a pharmaceutically acceptable salt thereof, wherein the cancer is selected from the group consisting of lung cancer, pancreatic cancer, cervical cancer, esophageal cancer, endometrial cancer, ovarian cancer, cholangiocarcinoma, and colorectal cancer.

15. The method according to claim 14 wherein the cancer is non-small cell lung cancer, and wherein one or more cells express KRas G12C mutant protein.

16. The method according to claim 14 wherein the cancer is colorectal cancer, and wherein one or more cells express KRas G12C mutant protein.

17. The method according to claim 14 wherein the cancer is pancreatic cancer, and wherein one or more cells express KRas G12C mutant protein.

18. The method according to claim 14 wherein the patient has a cancer that was determined to have one or more cells expressing the KRas G12C mutant protein prior to administration of the compound or a pharmaceutically acceptable salt thereof.

19. A method of treating a patient with a cancer that has a KRAS G12C mutation comprising administering to a patient in need thereof an effective amount of a compound according to claim 1, or a pharmaceutically acceptable salt thereof.

20. The method according to claim 14, wherein the patient is also administered an effective amount of one or more of a PD-1 inhibitor, a PD-L1 inhibitor, a CDK4/CDK6 inhibitor, or a pharmaceutically acceptable salt thereof, an EGFR inhibitor, or a pharmaceutically acceptable salt thereof, an ERK inhibitor, or a pharmaceutically acceptable salt thereof, a platinum agent, and or pemetrexed, or a pharmaceutically acceptable salt thereof.

21. The compound, or a pharmaceutically acceptable salt thereof, according to claim 1, for use in therapy.

22. The compound, or a pharmaceutically acceptable salt thereof, according to claim 1, for use in the treatment of cancer.

23. The compound, or a pharmaceutically acceptable salt thereof, for use according to claim 22, wherein the cancer is selected from the group consisting of lung cancer, pancreatic cancer, cervical cancer, esophageal cancer, endometrial cancer, ovarian cancer, cholangiocarcinoma, and colorectal cancer.

24. The compound, or a pharmaceutically acceptable salt thereof, according to claim 1 for use in simultaneous, separate or sequential combination with one or more of a PD-1 or PD-L1 inhibitor; a CDK4/CDK6 inhibitor, or a pharmaceutically acceptable salt thereof; an EGFR inhibitor, or a pharmaceutically acceptable salt thereof; an ERK inhibitor, or a pharmaceutically acceptable salt thereof; a platinum agent; and or pemetrexed, or a pharmaceutically acceptable salt thereof, in the treatment of cancer.

* * * * *